(12) United States Patent
Gopalsamy et al.

(10) Patent No.: US 7,388,016 B2
(45) Date of Patent: Jun. 17, 2008

(54) DIBENZONAPHTHYRIDINE DERIVATIVES AND METHODS OF USE THEREOF

(75) Inventors: Ariamala Gopalsamy, Mahwah, NJ (US); Mengxiao Shi, New Rochelle, NY (US); Kristina Kutterer, Westwood, NJ (US); Kim Timothy Arndt, Towaco, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/634,601

(22) Filed: Dec. 6, 2006

(65) Prior Publication Data

US 2007/0135429 A1  Jun. 14, 2007

Related U.S. Application Data

(60) Provisional application No. 60/750,145, filed on Dec. 13, 2005, provisional application No. 60/857,411, filed on Nov. 7, 2006.

(51) Int. Cl.
*A61K 31/4745* (2006.01)
*C07D 471/04* (2006.01)

(52) U.S. Cl. .................. 514/285; 546/70; 544/125; 544/361; 514/232.8; 514/253

(58) Field of Classification Search ............. 514/285, 514/232.8, 253; 546/70; 544/125, 361
See application file for complete search history.

(56) References Cited

U.S. PATENT DOCUMENTS

| 3,710,795 A | 1/1973 | Higuchi et al. |
| 3,993,656 A | 11/1976 | Rooney et al. |
| 5,262,564 A | 11/1993 | Kun et al. |

FOREIGN PATENT DOCUMENTS

| WO | WO-03/018579 A1 | 3/2003 |
| WO | WO-03/101927 | 12/2003 |
| WO | WO-2005/044130 A1 | 5/2005 |

OTHER PUBLICATIONS

Gopalsamy, A. et al.: Discovery of Dibenzo[c,f][2,7] naphthyridines as potent and selective 3-phosphoinositide-dependent kinase-1 inhibitors. J. Med. Chem., vol. 50, pp. 5547-5549, 2007.*
Arauzo-Bravo, M. J. and K. Shimizu. "An improved method for statistical analysis of metabolic flux analysis using isotopomer mapping matrices with analytical expressions." J. Biotech., 105:117-133. (2003).
Bloomfield, Derek G. et al. "Cyclic Amidines Part 25. Intramolecular Cyclodehalogenation of Diazabenz[a]anthracenes and Diazbenzo[c]phenanthrenes." J. Chem. Soc. Perkin Trans. 1, (6): 857-860 (1986).
Boschelli, D. H. and F. Ye. "Preparation of a series of benzothieno[3,2-b] pyridine-3-carbonitriles and benzofuro[3,2-b] pyridine-3-carbonitriles." J. Het. Chem., 39:783-788. (2002).

Boschelli, D. H. et al. "Synthesis and src kinase inhibitory activity of 2-phenyl- and 2-thienyl-7-phenylaminothieno[3,2-b]pyridine-6-carbontriles." J. Med. Chem., 48:3891-3902 (2005).
Bradley, William and Robert Robinson. "The Hydrolytic Fission of Some Substituted Dibenzoylmethanes." J. Chem. Soc. 2356-2367. (1926).
Chen, J. J. et al. "Rapid improvement of a reductive sulfonylation using design of experiement methods." Org. Proc. Res. Dev., 7:313-317. (2003).
English Abstract of: Colonge, Jean et al. "Syntheses a partir du dimere de l'acrolelne." Bulletin de La Societe Chimique de France. (6): 1288-1292. (1963).
Colonge, Jean et al. "Syntheses a partir du dimere de l'acrolelne." Bulletin de La Societe Chimique de France. (6): 1288-1292. (1963).
Dal Maso et al. "Epidemiology of non-Hodgkin lymphomas and other haemolymphopoietic neoplasms in people with AIDS." Lancet Oncol., 4(2):110-119. (2003).
El-Serag. "*Hepatocellular Carcinoma.* An Epidemiologic View." J. Clin. Gastroenterol., 35(5 Suppl. 2):S72-S78. (2002).
Elnatan, J. et al. "HIT family genes: FHIT but not PKCI-1/HINT produces altered transcripts in colorectal cancer." Br. J. Cancer, 81(5):874-880. (1990).
Gooding, O. W. "Process optimization using combinatorial design principles: parallel synthesis and design of experiment methods." Curr. Opinion. Chem. Biol., 8:297-304. (2004).
Gulland, John Masson and Robert Robinson. "Synthetical Experiments in the Napthyridine Groups." J. Chem. Soc. 127: 1493-1503. (1925).
Halliwell, C. M. and A. E. Cass. "A factorial analysis of silanization conditions for the immobilization of the oligonucleotides on glass surfaces." Anal. Chem., 73:2476-2483. (2001).
Hernandez-Avila et al. "Human Papilloma Virus 16-18 Infection and Cervical Cancer in Mexico: A Case-Control Study." Archives of Medical Research, 28:265-271. (1997).
Herrmann et al. "Epstein-Barr virus-associated carcinomas: facts and fiction." J. Pathol., 199(2):140-145. (2003).
Jaeda, M. I. et al. "Synthesis of Some Novel Dibenzo[c,f][2,7]naphthyridine Derivatives as Possible Antitumor Agents." The Chinese Pharmaceutical Journal, 42(5):403-409. (1990).
Kadow et al. "The role of viruses in human cancer development and antiviral approaches for intervention." Curr. Opin. Investig. Drugs, 3(11):1574-1579. (2002).
Kobayashi et al. "Activation of serum-and glucocorticoid-regulated protein kinase by agonists that activate phosphatidylinositide 3-kinase is mediated by 3-phosphoinositide-dependent protein kinase-2 (PDK1) and PDK2." Biochem J., 339:319-328. (1999).
Lawson, Wilfred et al. "Harmine and Harmaline. Part VII. A Synthesis of apoHarmine and of certain Carboline and Copyrine Derivatives." J. Chem. Soc. 125: 626-657. (1923).

(Continued)

*Primary Examiner*—Charanjit S Aulakh
(74) *Attorney, Agent, or Firm*—Daniel B. Moran

(57) ABSTRACT

The present invention relates to Dibenzonaphthyridine Derivatives, compositions comprising an effective amount of a Dibenzonaphthyridine Derivative and methods for treating or preventing a proliferative disorder, comprising administering to a subject in need thereof an effective amount of a Dibenzonaphthyridine Derivative.

37 Claims, No Drawings

OTHER PUBLICATIONS

Le Mapihan, K. et al. "Reversed-phase liquid chromatography column testing; robustness study of the test." J. Chrom. A., 1061:149-158. (2004).

March. "Advanced Organic Chemistry: Reactions, Mechanisms and Structure." Fourth Edition, John Wiley and Sons. pp. 635-637. (1992).

Morris, N. D. and T. E. Mallouk. "A high-throughput optical screening method for the optimization of colloidal water oxidation catalysts." J. Am. Chem. Soc., 124:11114-11121. (2002).

Mortreux et al. "Molecular and cellular aspects of HTLV-1 associated leukemogenesis in vivo." Leukemia, 17(1):26-38. (2003).

Parfitt, Robert T. "Benzo[a][3,6]phenanthrolines." J. Med. Chem. (9): 161-162. (1966).

Park et al. "Serum and glucocorticoid-inducible kinase (SGK) is a target of the Pl 3-kinase-stimulated signaling pathway." EMBO J., 18:3024-3033. (1999).

Partridge, M. W. and H. J. Vipond. "3,6-Phenanthrolines Derived from 2,2'-Diaminobenzophenone." J. Chem. Soc. 632-635. (1961).

Search Report No. 92005, Chemical Information Sciences. May 18, 2005.

Stazi, F. et al. "Accelerated Koenigs-Knorr Glucuronidation of a Deactivated Nitrophenol: Unveiling the Role of Polyamine Additive1,1,4,7,10, 10-Hexamethyltriethylenetetramine through Design of Experiments." J. Org. Chem., 69:1097-1103. (2004).

Tucker, Sheryl A. and William E. Acree. "Polycyclic Aromatic Nitrogen Heterocycles. Part VI. Fluorescence Emission and Quenching Behavior of Select Phenyl-and Alkyl-derivatives Dissolved in Nonelectrolyte Solvents." Polycyclic Aromatic Compounds, 3:221-229. (1993).

Tucker, Sheryl A. et al. "Polycyclic Aromatic Nitrogen Heterocycles. Part V: Fluorescence Emission Behavior of Select Tetraaza- and Diazaarenes in Nonelectrolyte Solvents." (Sep. 1992).

Upton, Christopher. "Cyclic Amidines. Part 26. The Reported Syntheses of 7-Anilino-6-aryl,5,12-diazabenz[a]anthracenes are Reinvestigaged and their Correct Structures Identified." J. Chem. Soc., Perkins Trans., pp. 1225-1229. (1986).

Upton, Mathew and Christopher Upton. "Novel nitrated derivatives of 5,8-diazabenzo[c]phenanthrene and 9,14-diazadibenz[a,e]acephenanthrylene: new classes of potent mutagenic compounds." Mutagenesis, 14(6):587-593. (1999).

Upton, Mathew et al. "Novel 5,8-Diazabenzo[c]phenanthrenes: Synthesis and Mutagenicity." J. Pharm. Pharmacol., 50(5):475-482. (1998).

Vijayalakshmi, S. and S. P. Rajendran. "A New Synthesis of 6,7-Dichloro-Dibenzo[c,f][2,7]-Naphthyridines via Photocyclization." OPPI Briefs, 30(3):356-359. (1998).

Walser, A. et al. "Nucleophilic Displacement of Aromatic Fluorine. Part IV. Quinolinoquinolines and Benzochromenoquinolines (1)." pp. 737-741. (Aug. 1975).

Wang, Y. D. et al. "A facile one-pot synthesis of 2-substituted-3-aminoquinolines:preparation of benzo[b]naphthyridine-3-carbonitriles." Tetrahedron, 60:2937-2942. (2004).

Wissner, A. et al. "Synthesis and structure-activity relationships of 6,7-Disubstituted 4-anilinoquinoline-3-carbonitriles. The design of an orally active, irreversible inhibitor of the tyrosine kinase activity of the epidermal growth factor receptor (EGFR) and the human Epidermal growth factor receptor-2 (HER-2)." J. Med. Chem., 46:49-63. (2003).

Bayascas, Jose R. et al. "Hypomorphic Mutation of PDK1 Suppresses Tumorigensis in PTEN+/− Mice," Current Biology, 15:1839-1846 (Oct. 25, 2005).

Feldman, Richard et al. "Novel Small Molecule Inhibitors of 3-Phosphoinositide-dependent Kinase-1," The Journal of Biological Chemistry, 280:19867-19874 (May 20, 2005).

Moran, Amy E. et al. "Apc Defiiciency Is Associated with Increased Egfr Activity in the Intestinal Enterocytes and Adenomas of C57BL/6J-Min/= Mice," The Journal of Biological Chemistry, 279(41):43261-43272 (2004).

Xie, Zhihui et al. "Transformation of Mammary Epithelial Cells by 3-Phosphoinositide-dependent Protein Kinase-1 Activates beta-Catenin and c-Myc, and Down-Regulates Caveolin-1," Cancer Research, 63:5370-5375 (Sep. 1, 2003).

Sato, Saori et al. "Interference with PDK-1 Akt survival signaling pathway by UCN-01 (7-hydroxystaurosporine," Oncogene 21:1727-1738 (2002).

Dasmahapatra, Girija P. et al. "In vitro Combination Treatment with Perifosine and UCN-01 Demonstrates Synergism against Prostate (PC-3) and Lung (A549) Epithelial Adenocarcinoma Cell Lines," Clinical Cancer Research 10:5242-5252 (Aug. 1, 2004).

Arico, Sebastien et al. "Celecoxib Induces Apoptosis by Inhibiting 3-Phosphoinositide-dependent Protein Kinase-1 Activity in the Human Colon Cancer HT-29 Cell Line," The Journal of Biological Chemistry 277(31):27613-27621 (Aug. 2, 2002).

Williams, Christopher S. et al. "Celecoxib Prevents Tumor Growth in Vivo without Toxicity to Normal Gut: Lack of Correlation between in Vitro and in Vivo Models," Cancer Research 60:6045-6051 (Nov. 1, 2000).

Database CA [Online] Chemical Abstracts, Columbus, Ohio, US; 1991, Jaeda, M. I. et al., "Synthesis of some novel dibenzoic[c,f][2,7] naphthyridine derivatives as possible antitumor agents," retrieved from STN Database accession No. 1991:143181, abstract, & Zhonghua Yaoxue Zazhi, 42(5), 403-10, Coden: Cyhcex; ISSN: 1016-1015, 1990.

Database CA [Online] Chemical Abstracts Service, Columbus, Ohio, US; 1999; Upton, Mathew et al.: "Novel nitrated derivatives of 5,8-diazabenzo[c]phenanthrene and 9, 14-diazadibenz[a,e]acephenanthrylene: new classes of potent mutagenic compounds," retrived from STN, Database accession No. 1999:789239 abstract & Mutagenesis, 14(6), 587-593 Coden: Mutaex; ISSN: 0267-8357, 1999.

Database CA [Online] Chemical Abstracts Service, Columbus, Ohio, US; 1998, Vijayalakhmi, S. et al: "A new synthesis of 6,7-dicholorodibenzo[c,f][2,7]naphthyridines via photocyclization," retrived from STN, Database accession No. 1998:383203 abstract & Organic Preparations and Procedures International, 30(3), 356-359 Coden: Oppiak; ISSN: 0030-4948, 1998.

Database CA [Online] Chemical Abstracts Service, Columbus, Ohio, US, 1998, Upton, Mathew et al: "Novel 5,8-diazabenzo[c]phenanthrenes: synthesis and mutagenicity," retrived from STN Database accession No. 1998:347644 abstract & Journal of Pharmacy and Pharmacology, 50(5), 475-482 Coden: JPPMAB; ISSN: 0022-3573, 1998.

Copy of International Search Report and Written Opinion issued for International Patent Application No. PCT/US2006/046646.

* cited by examiner

DIBENZONAPHTHYRIDINE DERIVATIVES AND METHODS OF USE THEREOF

This application claims priority from United States Provisional Application No. 60/857,411, filed Nov. 7, 2006, and from United States Provisional Application No. 60/750,145, filed Dec. 13, 2005, the entire disclosures of each of which are hereby incorporated by reference in their entirety.

1. FIELD OF THE INVENTION

The present invention relates to Dibenzonaphthyridine Derivatives, compositions comprising an effective amount of a Dibenzonaphthyridine Derivative and methods for treating or preventing a proliferative disorder, comprising administering to a subject in need thereof an effective amount of a Dibenzonaphthyridine Derivative.

2. BACKGROUND OF THE INVENTION

Cancer is second only to cardiovascular disease as a cause of death in the United States. The American Cancer Society estimated that in 2004, there were 1.6 million new cases of cancer and 655,000 cancer-related deaths. There are currently over 10 million living Americans who have been diagnosed with cancer and the NIH estimates the direct medical costs of cancer as over $100 billion per year with an additional $100 billion in indirect costs due to lost productivity—the largest such costs of any major disease.

Cancer is a process by which the controlling mechanisms that regulate cell growth and differentiation are impaired, resulting in a failure to control cell turnover and growth. This lack of control causes a tumor to grow progressively, enlarging and occupying space in vital areas of the body. If the tumor invades surrounding tissue and is transported to distant sites, death of the individual can result.

The selective killing of cancer cells, while minimizing deleterious effects on normal cells, is a desired goal in cancer therapy. Modalities commonly used in the treatment of cancer include chemotherapy, radiation therapy, surgery and biological therapy (a broad category that includes gene-, protein- or cell-based treatments and immunotherapy). Despite the availability of a variety of anticancer agents, traditional chemotherapy has drawbacks. Many anticancer agents are toxic, and chemotherapy can cause significant, and often dangerous, side effects, including severe nausea, bone marrow depression, liver, heart and kidney damage, and immunosuppression. Additionally, many tumor cells eventually develop multi-drug resistance after being exposed to one or more anticancer agents. As such, single-agent chemotherapy is effective for only a very limited number of cancers. Many chemotherapeutic drugs are anti-proliferative agents, acting at different stages of the cell cycle. Since it is difficult to predict the pattern of sensitivity of a neoplastic cell population to anticancer drugs, or the current stage of the cell cycle that a cell happens to be in, it is common to use multi-drug regimens in the treatment of cancer.

Despite the significant research efforts and resources which have been directed towards the development of novel anticancer agents and improved methods for treating cancer there remains a need in the art for novel compounds, compositions, and methods that are useful for treating cancer with improved therapeutic indices.

3. SUMMARY OF THE INVENTION

In one aspect the invention provides a compound of Formula (I):

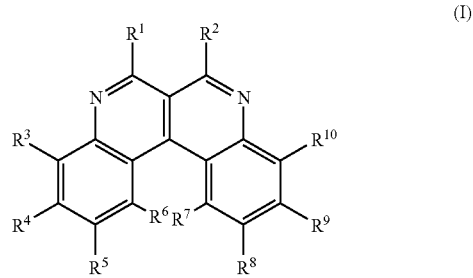

or a pharmaceutically acceptable salt thereof,
wherein
$R^1$ is —H, —OH, —O—$C_1$-$C_6$ alkyl, -halo, —$C_2$-$C_6$ alkenyl, —$C_2$-$C_6$ alkynyl, —N($R^{18}$)$_2$, —NH—O$R^{18}$ or —C(O)N($R^{18}$)$_2$;
$R^2$ is —H, —O—$C_1$-$C_6$ alkyl, -halo, —$C_2$-$C_6$ alkenyl, —$C_2$-$C_6$ alkynyl, —NH$R^{17}$, —N($R^{17}$)$_2$, —NH—O$R^{18}$ or —C(O)N($R^{18}$)$_2$, such that when $R^1$ is —OH or —O—$C_1$-$C_6$ alkyl, $R^2$ is hydrogen;
$R^3$, $R^4$, $R^5$, $R^6$, $R^7$, $R^8$, $R^9$ and $R^{10}$ are each independently —H, -halo, —OH, —SH, —N($R^{12}$)$_2$, —NHO$R^{12}$, —CN, —NO$_2$, —CF$_3$, —OCF$_3$, —$C_1$-$C_6$ alkyl, —$C_2$-$C_6$ alkenyl, —$C_2$-$C_6$ alkynyl, —$C_3$-$C_8$ cycloalkyl, —$C_3$-$C_8$ cycloalkenyl, -phenyl, -benzyl, —(CH$_2$)$_n$—O—$C_1$-$C_6$ alkyl, —O—$C_2$-$C_6$ alkenyl, —O—$C_2$-$C_6$ alkynyl, —O-phenyl, —S-phenyl, —NH—$C_1$-$C_6$ alkyl, —(CH$_2$)$_n$—C(O)—$R^{11}$, —(CH$_2$)$_n$—OC(O)—$R^{11}$, —(CH$_2$)$_n$—NHC(O)—$R^{11}$, —S—$C_1$-$C_6$ alkyl, —S(O)—$C_1$-$C_6$ alkyl, —SO$_2$—$C_1$-$C_6$ alkyl, —SO$_2$NH—$C_1$-$C_6$ alkyl, —SO$_2$NH—$C_2$-$C_6$ alkenyl, —SO$_2$NH—$C_2$-$C_6$ alkynyl, —Y—(CH$_2$)$_k$-M-CH($R^{14}$)$R^{15}$, —Y—(CH$_2$)$_g$—$R^{16}$, —Y—(CH$_2$)$_k$-M-(CH$_2$)$_p$—$R^{16}$, —Y—(CH$_2$)$_k$—(W)$_a$—(CH$_2$)$_q$—Z, —Y—(CH$_2$)$_p$—(Z)$_a$-(CH$_2$)$_q$—Z, or

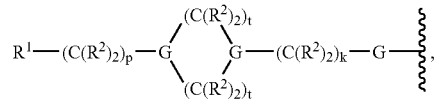

such that $R^3$, $R^4$, $R^5$, $R^6$, $R^7$, $R^8$, $R^9$ and $R^{10}$ are not simultaneously hydrogen;
$R^{11}$ is —H, —$C_1$-$C_6$ alkyl, —$C_2$-$C_6$ alkenyl, —$C_2$-$C_6$ alkynyl, -phenyl, —O—$C_1$-$C_6$ alkyl, —O—$C_2$-$C_6$ alkenyl, —O—$C_2$-$C_6$ alkynyl, —O-phenyl, —S-phenyl, —S—$C_1$-$C_6$ alkyl or —N($R^{12}$)$_2$;
each occurrence of $R^{12}$ is independently —H, —$C_1$-$C_6$ alkyl, —$C_2$-$C_6$ alkenyl, —$C_2$-$C_6$ alkynyl, -phenyl or -benzyl;
each occurrence of G is independently —O—, —S—, —(CH$_2$)—,

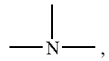

or —N(R$^{13}$)—;

M is —O—, —N(R$^{13}$)—, —N((C(R$^{13}$)$_2$)$_p$N(R$^{13}$)$_2$)— or —N((C(R$^{13}$)$_2$)$_p$—OR$^{13}$)—;

W is —O— or —N(R$^{13}$)—;

Y is —O—, —S—, —(CH$_2$)$_a$— or —N(R$^{13}$)—;

Z is a -3- to 7-membered non-aromatic monocyclic heterocycle, -5- or 6-membered aromatic monocyclic heterocycle, or -8- to 12-membered bicyclic heterocycle, wherein a -3- to 7-membered non-aromatic monocyclic heterocycle may be unsubstituted or independently substituted on a ring carbon or ring nitrogen atom with one or more of —R$^{13}$, —N(R$^{13}$)$_2$, —OH, —OR$^{13}$, —(C(R$^{13}$)$_2$)$_s$OR$^{13}$ or —(C(R$^{13}$)$_2$)$_s$N(R$^{13}$)$_2$;

each occurrence of R$^{13}$ is independently —H, —C$_1$-C$_6$ alkyl, —CH$_2$—C$_2$-C$_6$ alkenyl, —CH$_2$—C$_2$-C$_6$ alkynyl, —C$_3$-C$_8$ cycloalkyl, —C$_3$-C$_8$ cycloalkenyl, -phenyl, —C(O)—C$_1$-C$_6$ alkyl or —C(O)—O—C$_1$-C$_6$ alkyl, such that when R$^{13}$ is phenyl, the phenyl group may be unsubstituted or independently substituted with one or more of —OH, —CN, —NO$_2$, —CF$_3$, —C$_1$-C$_6$ alkyl, —NH(C$_1$-C$_3$ alkyl), —N(C$_1$-C$_3$ alkyl)$_2$, —(CH$_2$)$_a$-halo, —(CH$_2$)$_a$—O—C$_1$-C$_6$ alkyl, —(CH$_2$)$_a$—O—C(O)C$_1$-C$_6$ alkyl, —S—C$_1$-C$_6$ alkyl, —C(O)OH, —C(O)O—C$_1$-C$_6$ alkyl, —S-phenyl, —O-phenyl, -phenyl, -benzyl, —NH—(CH$_2$)$_a$-phenyl or —NHC(O)C$_1$-C$_6$ alkyl;

R$^{14}$ is —H, —(C(R$^{13}$)$_2$)$_r$N(R$^{13}$)$_2$ or —(C(R$^{13}$)$_2$)$_r$OR$^{13}$;

R$^{15}$ is —H, —(C(R$^{13}$)$_2$)$_r$N(R$^{13}$)$_2$ or —(C(R$^{13}$)$_2$)$_r$OR$^{13}$;

R$^{16}$ is —H, -halo, —N(R$^{13}$)$_2$, —OR$^{13}$, —N(R$^{13}$)$_3^+$ or —N(R$^{13}$)—OR$^{13}$;

each occurrence of R$^{17}$ is independently —C$_1$-C$_6$ alkyl, —C$_2$-C$_6$ alkenyl, —C$_2$-C$_6$ alkynyl, -phenyl or benzyl;

each occurrence of R$^{18}$ is independently —H, —C$_1$-C$_6$ alkyl, —C$_2$-C$_6$ alkenyl, —C$_2$-C$_6$ alkynyl, -phenyl or benzyl;

a is 0 or 1;

g is an integer ranging from 1 to 6;

k is an integer ranging from 1 to 4;

n is an integer ranging from 0 to 6;

p is an integer ranging from 1 to 4;

q is an integer ranging from 0 to 4;

r is an integer ranging from 1 to 4;

s is an integer ranging from 1 to 6; and each occurrence of t is independently an integer ranging from 1 to 3.

Compounds of Formula (I) or a pharmaceutically acceptable salt thereof (a "Dibenzonaphthyridine Derivative") are useful for treating or preventing a proliferative disorder.

The invention provides methods for treating or preventing a proliferative disorder, comprising administering to a subject in need of such treatment or prevention an effective amount of a Dibenzonaphthyridine Derivative.

The invention further provides compositions comprising an effective amount of a Dibenzonaphthyridine Derivative and a physiologically acceptable carrier or vehicle.

The details of the invention are set forth in the accompanying description below. All references cited in this specification are herein incorporated by reference in their entirety.

4. DETAILED DESCRIPTION OF THE INVENTION

4.1 Definitions and Abbreviations

The following definitions are used in connection with the Dibenzonaphthyridine Derivatives:

"C$_1$-C$_6$ alkyl" refers to a straight or branched chain saturated hydrocarbon containing 1-6 carbon atoms. Representative C$_1$-C$_6$ alkyl groups include, but are not limited to, methyl, ethyl, propyl, isopropyl, butyl, tert-butyl, sec-butyl, isobutyl, pentyl, isopentyl, neopentyl, hexyl, isohexyl and neohexyl. In one embodiment, the C$_1$-C$_6$ alkyl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_1$-C$_6$ alkyl group is unsubstituted.

"C$_2$-C$_6$ alkenyl" refers to a straight or branched chain unsaturated hydrocarbon containing 2-6 carbon atoms and at least one double bond. Representative C$_2$-C$_6$ alkenyl groups include, but are not limited to, ethylene, propylene, 1-butylene, 2-butylene, isobutylene, sec-butylene, 1-pentene, 2-pentene, isopentene, 1-hexene, 2-hexene, 3-hexene and isohexene. In one embodiment, the C$_2$-C$_6$ alkenyl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_2$-C$_6$ alkenyl group is unsubstituted.

"C$_2$-C$_6$ alkynyl" refers to a straight or branched chain unsaturated hydrocarbon containing 2-6 carbon atoms and at least one triple bond. Representative C$_2$-C$_6$ alkynyl groups include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne and isohexyne. In one embodiment, the C$_2$-C$_6$ alkenyl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_2$-C$_6$ alkenyl group is unsubstituted.

"Halo" refers to —F, —Cl, —Br or —I.

A "C$_3$-C$_8$ monocyclic cycloalkyl" is a non-aromatic, saturated hydrocarbon ring containing 3-8 carbon atoms. Representative C$_3$-C$_8$ monocyclic cycloalkyl groups include, but are not limited to, cyclopropyl, cyclobutyl, cyclopentyl, cyclohexyl, cycloheptyl and cyclooctyl. In one embodiment, the C$_3$-C$_8$ monocyclic cycloalkyl group is substituted with one or more of the following groups: —C$_1$-C$_6$ alkyl, -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_3$-C$_8$ monocyclic cycloalkyl group is unsubstituted.

A "C$_3$-C$_8$ monocyclic cycloalkenyl" is a non-aromatic hydrocarbon ring containing 3-8 carbon atoms and having at least one endocyclic double bond. Representative C$_3$-C$_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, -1,3,5-cycloheptatrienyl, cyclooctenyl, 1,3-cyclooctadienyl, 1,4-cyclooctadienyl, -1,3,5-cyclooctatrienyl. In one embodiment, the C$_3$-C$_8$ monocyclic cycloalkenyl group is substituted with one or more of the following groups: —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl group is unsubstituted.

The term "3- to 7-membered non-aromatic monocyclic heterocycle" refers to (1) a 3- or 4-membered non-aromatic monocyclic cycloalkyl in which one of the ring carbon atoms has been replaced with a N, O or S atom; or (2) a 5-, 6-, or 7-membered non-aromatic monocyclic cycloalkyl in which 1 to 3 of the ring carbon atoms has been independently replaced with an N, O or S atom. In one embodiment, a carbon atom of a 3- to 7-membered heterocycle is replaced with a carbonyl group. A 3- to 7-membered non-aromatic monocyclic heterocycle can be attached via a ring nitrogen or ring carbon atom. Representative examples of a 3- to 7-membered non-aromatic monocyclic heterocycle group include, but are not limited to azepanyl, aziridinyl, 1,3-dioxolanyl, 1,4-dioxolanyl, imidazolidinyl, imidazolinyl, morpholinyl, piperazinyl, N-methylpiperazinyl, piperidinyl, N-methylpiperidinyl, pyranyl, pyrazolidinyl, pyrazolinyl, pyrrolidinonyl, pyrrolidinyl, N-methylpyrrolidinyl, N-benzylpyrrolidinyl, pyrrolinyl, tetrahydrofuranyl, tetrahydropyranyl, thiomorpholinyl and trithianyl. In one embodiment, the 3- to 7-membered non-aromatic monocyclic heterocycle group is indepenedently substituted on one or more ring nitrogen or ring carbon atoms with one or more of the following groups: —$R^{13}$, —N($R^{13}$)$_2$, —OH, —O$R^{13}$, —(C($R^{13}$)$_2$)$_s$O$R^{13}$ or —(C($R^{13}$)$_2$)$_s$N($R^{13}$)$_2$, wherein $R^{13}$ and s are as defined above for the compounds of formula (I). In another embodiment, the 3- to 7-membered non-aromatic monocyclic heterocycle group is unsubstituted.

The term "5- or 6-membered aromatic monocyclic heterocycle" refers to a 5- or 6-membered aromatic monocyclic cycloalkyl in which from 1 to 4 of the ring carbon atoms has been replaced with an N, O or S atom. The 5- or 6-membered aromatic monocyclic heterocycles are attached via a ring carbon atom. Representative examples of a 5- or 6-membered aromatic monocyclic heterocycle group include, but are not limited to furanyl, imidazolyl, isothiazolyl, isoxazolyl, oxazolyl, oxadiazolyl, pyrimidinyl, pyrazolyl, pyrazinyl, pyridazinyl, pyridinyl, pyrrolyl, thiazolyl, thiadiazolyl, thiophenyl, triazinyl, and triazolyl. In one embodiment, the 5- or 6-membered aromatic monocyclic heterocycle group is independently substituted with one or more of the following groups: —$R^{13}$, —N($R^{13}$)$_2$, —OH, —O$R^{13}$, —(C($R^{13}$)$_2$)$_s$O$R^{13}$ or —(C($R^{13}$)$_2$)$_s$N($R^{13}$)$_2$, wherein $R^{13}$ and s are as defined above for the compounds of formula (I). Unless indicated, the 5- or 6-membered aromatic monocyclic heterocycle group is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 1-4 of it's ring carbon atoms independently replaced with a N, O or S atom. Included in this class are 3- to 7-membered monocyclic heterocycles that are fused to a benzene ring. A non-aromatic ring of an 8- to 12-membered monocyclic heterocycle is attached via a ring nitrogen or ring carbon atom. An aromatic 8- to 12-membered monocyclic heterocycles is attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of the 8- to 12-membered bicyclic heterocycle group can substituted with one or more of the following groups: —$R^{13}$, —N($R^{13}$)$_2$, —OH, —O$R^{13}$, —(C($R^{13}$)$_2$)$_s$O$R^{13}$ or —(C($R^{13}$)$_2$)$_s$N($R^{13}$)$_2$, wherein $R^{13}$ and s are as defined above for the compounds of formula (I). Unless indicated, the 8- to 12-membered bicyclic heterocycle group is unsubstituted.

A "subject" is a mammal, e.g., a human, mouse, rat, guinea pig, dog, cat, horse, cow, pig, or non-human primate, such as a monkey, chimpanzee, baboon. In one embodiment, the monkey is a rhesus. In one embodiment, a subject is a human.

The phrase "pharmaceutically acceptable salt," as used herein, is a salt formed from an acid and a basic nitrogen group of one of the Dibenzonaphthyridine Derivatives. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, besylate, mesylate, camphor sulfonate, and pamoate (i.e., 1,1'-methylene-bis-(2-OH-3-naphthoate)) salts.

The term "pharmaceutically acceptable salt" also refers to a salt prepared from a Dibenzonaphthyridine Derivative having an acidic functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, tris-(hydroxymethyl)methylamine, or 2-hydroxy-tert-butylamine, or N,N-di-lower alkyl-N-(hydroxy lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. A hydrate is another example of a pharmaceutically acceptable salt.

An "effective amount" when used in connection with a Dibenzonaphthyridine Derivative is an amount effective for treating or preventing a proliferative disorder.

An "effective amount" when used in connection with another anticancer agent is an amount that is effective for treating or preventing cancer alone or in combination with a Dibenzonaphthyridine Derivative.

"In combination with" includes administration within the same composition and within separate compositions. In the latter instance, the anticancer agent is administered during a time when the Dibenzonaphthyridine Derivative exerts its prophylactic or therapeutic effect, or vice versa.

Some chemical structures herein are depicted using bold and dashed lines to represent chemical bonds. These bold and dashed lines depict absolute stereochemistry.

Illustrative examples of the Dibenzonaphthyridine Derivatives are described herein using both chemical structures and chemical names.

The following abbreviations are used herein and have the indicated definitions: BOC is tert-butyl carbamate, BSA is bovine serum albumin, DIBAL is diisobutylaluminum hydride, DME is dimethoxyethane, DMF is N,N-dimethylformamide, DMSO is dimethylsulfoxide, Et is ethyl, EtOAc is ethyl acetate, EtOH is ethanol, HPLC is high performance liquid chromatography, Me is methyl, MS is mass spectrometry, NMP is N-methylpyrrolidone, NMR is nuclear magnetic resonance, PBS is phosphate-buffered saline (pH 7.4), and Ph is phenyl.

4.2 The Dibenzonaphthyridine Derivatives of Formula (I)

The present invention provides Dibenzonaphthyridine Derivatives according to Formula (I), below:

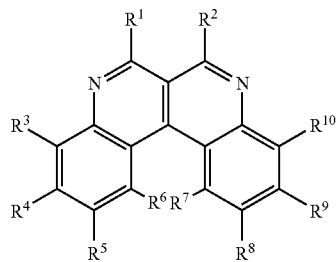

(I)

and pharmaceutically acceptable salts thereof,
wherein
$R^1$, $R^2$, $R^3$, $R^4$, $R^5$, $R^6$, $R^7$, $R^8$, $R^9$ and $R^{10}$ are as defined above for the compounds of formula (I).

In one embodiment, $R^1$ is —OH, —O—$C_1$-$C_6$ alkyl, -halo, —$C_2$-$C_6$ alkenyl, —$C_2$-$C_6$ alkynyl, —N($R^{18}$)$_2$, —NH—O$R^{18}$ or —C(O)N($R^{18}$)$_2$.

In one embodiment, $R^1$ is —NH$_2$.
In another embodiment, $R^1$ is —NH($C_1$-$C_6$ alkyl).
In another embodiment, R is —H.
In one embodiment, $R^1$ is —NH$_2$ and $R^2$ is —H.
In another embodiment, $R^1$ is —NH($C_1$-$C_6$ alkyl) and $R^2$ is —H.
In a specific embodiment, $R^1$ is —NHCH$_3$.
In another specific embodiment, $R^1$ is —NHEt.
In another specific embodiment, $R^1$ is —OH and $R^2$ is —H.
In one embodiment, $R^1$ is —O—$C_1$-$C_6$ alkyl.
In a specific embodiment, $R^1$ is —OCH$_3$.
In another embodiment, $R^3$ is —$C_1$-$C_6$ alkyl.
In a specific embodiment, $R^3$ is —CH$_3$.
In another embodiment, $R^3$ is —H.
In still another embodiment, $R^3$ is -halo.
In a specific embodiment, $R^3$ is —Cl.
In yet another embodiment, $R^3$ is —O—$C_1$-$C_6$ alkyl.
In yet another embodiment, $R^3$ is —OCH$_3$.
In one embodiment, $R^4$ is —H.
In another embodiment, $R^4$ is —NH$_2$.

In another specific embodiment, $R^4$ is -phthalimid-1-yl.
In one embodiment, $R^8$ is —O—$C_1$-$C_6$ alkyl.
In a specific embodiment, $R^8$ is —OCH$_3$.
In one embodiment, $R^9$ is —O—$C_1$-$C_6$ alkyl.
In another embodiment, $R^9$ is —OCH$_3$ or —OEt.
In another embodiment, $R^9$ is -halo.
In a specific embodiment, $R^9$ is —F.
In one embodiment, at least one of $R^3$, $R^4$, $R^5$, $R^6$, $R^7$, $R^8$, $R^9$ and $R^{10}$ is
—Y—CH$_2$—Z—CH$_2$—Z, wherein Z is a substituted or unsubstituted -3- to 7-membered non-aromatic monocyclic heterocycle, -5- or 6-membered aromatic monocyclic heterocycle, or a -8- to 12-membered bicyclic heterocycle.

In one embodiment, at least one of $R^3$, $R^4$, $R^5$, $R^6$, $R^7$, $R^8$, $R^9$ and $R^{10}$ is

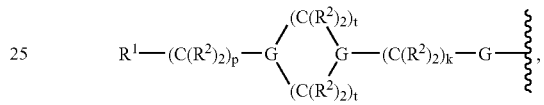

wherein $R^1$, $R^2$, G, k, p and t are as defined above for the compounds of formula (I).

In one embodiment, $R^1$, $R^2$, $R^3$, $R^4$, $R^5$, $R^6$, $R^7$, $R^8$, $R^9$ and $R^{10}$ are not simultaneously hydrogen.

In another embodiment, $R^9$ is —OCH$_2$-(-3- to 7-membered monocyclic non-aromatic heterocycle), —O(CH$_2$)$_2$-(-3- to 7-membered monocyclic non-aromatic heterocycle), —O(CH$_2$)$_2$($C_3$-$C_8$ cycloalkyl), or —O(CH$_2$)$_3$-(-3- to 7-membered monocyclic non-aromatic heterocycle).

In another embodiment, $R^9$ is —NHCH$_2$-(-3- to 7-membered monocyclic non-aromatic heterocycle), —NH(CH$_2$)$_2$-(-3- to 7-membered monocyclic non-aromatic heterocycle) or —NH(CH$_2$)$_3$-(-3- to 7-membered monocyclic non-aromatic heterocycle).

In another embodiment, $R^9$ is —N(CH$_3$)CH$_2$-(-3- to 7-membered monocyclic non-aromatic heterocycle), —N(CH$_3$)(CH$_2$)$_2$-(-3- to 7-membered monocyclic non-aromatic heterocycle) or —N(CH$_3$)(CH$_2$)$_3$-(-3- to 7-membered monocyclic non-aromatic heterocycle).

In one embodiment, $R^5$, $R^6$, $R^7$ and $R^{10}$ are each —H.
In another embodiment, $R^2$, $R^5$, $R^6$, $R^7$ and $R^{10}$ are each —H.
In another embodiment, $R^2$, $R^5$, $R^6$, $R^7$ and $R^{10}$ are each —H and $R^3$ is —$C_1$-$C_6$ alkyl,
In still another embodiment, $R^2$, $R^5$, $R^6$, $R^7$ and $R^{10}$ are each —H and $R^3$ is —CH$_3$.
In one embodiment, $R^2$, $R^5$, $R^6$, $R^7$ and $R^{10}$ are each —H, $R^3$ is —$C_1$-$C_6$ alkyl, and $R^4$ is —NH$_2$.
In a specific embodiment, $R^2$, $R^5$, $R^6$, $R^7$ and $R^{10}$ are each —H, $R^3$ is —CH$_3$, and $R^4$ is —NH$_2$.
In one embodiment, $R^2$, $R^5$, $R^6$, $R^7$ and $R^{10}$ each —H, $R^3$ is —$C_1$-$C_6$ alkyl, $R^4$ is —NH$_2$, and $R^8$ is —O—$C_1$-$C_6$ alkyl.
In a specific embodiment, $R^2$, $R^5$, $R^6$, $R^7$ and $R^{10}$ are each —H, $R^3$ is —CH$_3$, $R^4$ is —NH$_2$, and $R^8$ is —OCH$_3$.

Illustrative examples of the Dibenzonaphthyridine Derivatives of formula (I) include the compounds set forth below:

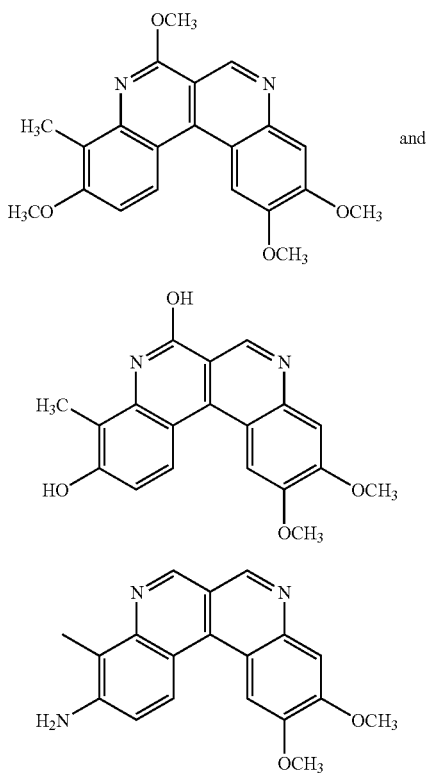

and pharmaceutically acceptable salts thereof.

In one embodiment, the compounds of formula (I) have the formula (Ia):

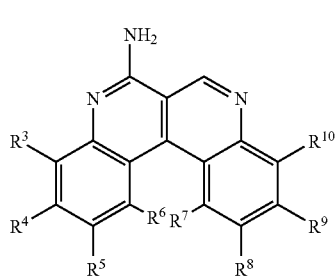

wherein $R^3$, $R^4$, $R^5$, $R^6$, $R^7$, $R^8$, $R^9$ and $R^{10}$ are as defined above for the compounds of formula (I).

In another embodiment, for the compounds of formula (Ia), $R^3$ is —$C_1$-$C_6$ alkyl.

In a specific embodiment, for the compounds of formula (Ia), $R^3$ is —$CH_3$.

In another embodiment, for the compounds of formula (Ia), $R^3$ is —H.

In still another embodiment, for the compounds of formula (Ia), $R^3$ is -halo.

In a specific embodiment, for the compounds of formula (Ia), $R^3$ is —Cl.

In yet another embodiment, for the compounds of formula (Ia), $R^3$ is —O—$C_1$-$C_6$ alkyl.

In yet another embodiment, for the compounds of formula (Ia), $R^3$ is —$OCH_3$.

In one embodiment, for the compounds of formula (Ia), $R^4$ is —H.

In a specific embodiment, for the compounds of formula (Ia), $R^4$ is —$NH_2$.

In another specific embodiment, for the compounds of formula (Ia), $R^4$ is -phthalimid-1-yl.

In another embodiment, for the compounds of formula (Ia), $R^4$ is —OH.

In still another embodiment, for the compounds of formula (Ia), $R^4$ is —O—$C_1$-$C_6$ alkyl.

In a specific embodiment, for the compounds of formula (Ia), $R^4$ is —$OCH_3$.

In one embodiment, for the compounds of formula (Ia), $R^8$ is —O—$C_1$-$C_6$ alkyl.

In a specific embodiment, for the compounds of formula (Ia), $R^8$ is —$OCH_3$.

In one embodiment, for the compounds of formula (Ia), $R^9$ is —O—$C_1$-$C_6$ alkyl.

In another embodiment, for the compounds of formula (Ia), $R^9$ is —$OCH_3$ or —OEt.

In another embodiment, for the compounds of formula (Ia), $R^9$ is -halo.

In a specific embodiment, for the compounds of formula (Ia), $R^9$ is —F.

In another embodiment, for the compounds of formula (Ia), $R^9$ is —$OCH_2$-(-3- to 7-membered monocyclic non-aromatic heterocycle), —$O(CH_2)_2$-(-3- to 7-membered monocyclic non-aromatic heterocycle), —$O(CH_2)_2(C_3$-$C_8$ cycloalkyl), or —$O(CH_2)_3$-(-3- to 7-membered monocyclic non-aromatic heterocycle).

In another embodiment, for the compounds of formula (Ia), $R^9$ is —$NHCH_2$-(-3- to 7-membered monocyclic non-aromatic heterocycle), —$NH(CH_2)_2$-(-3- to 7-membered monocyclic non-aromatic heterocycle) or —$NH(CH_2)_3$-(-3- to 7-membered monocyclic non-aromatic heterocycle).

In another embodiment, for the compounds of formula (Ia), $R^9$ is —$N(CH_3)CH_2$-(-3- to 7-membered monocyclic non-aromatic heterocycle), —$N(CH_3)(CH_2)_2$-(-3- to 7-membered monocyclic non-aromatic heterocycle) or —$N(CH_3)(CH_2)_3$-(-3- to 7-membered monocyclic non-aromatic heterocycle).

In one embodiment, for the compounds of formula (Ia), $R^5$, $R^6$, $R^7$ and $R^{10}$ are each —H.

In another embodiment, for the compounds of formula (Ia), $R^5$, $R^6$, $R^7$ and $R^{10}$ are each —H.

In another embodiment, for the compounds of formula (Ia), $R^5$, $R^6$, $R^7$ and $R^{10}$ are each —H and $R^3$ is —$C_1$-$C_6$ alkyl.

In still another embodiment, for the compounds of formula (Ia), $R^5$, $R^6$, $R^7$ and $R^{10}$ are each —H and $R^3$ is —$CH_3$.

In one embodiment, for the compounds of formula (Ia), $R^5$, $R^6$, $R^7$ and $R^{10}$ are each —H, $R^3$ is —$C_1$-$C_6$ alkyl, and $R^4$ is —$NH_2$.

In a specific embodiment, for the compounds of formula (Ia), $R^5$, $R^6$, $R^7$ and $R^{10}$ are each —H, $R^3$ is —$CH_3$, and $R^4$ is —$NH_2$.

In one embodiment, for the compounds of formula (Ia), $R^5$, $R^6$, $R^7$ and $R^{10}$ each —H, $R^3$ is —$C_1$-$C_6$ alkyl, $R^4$ is —$NH_2$, and $R^8$ is —O—$C_1$-$C_6$ alkyl.

In a specific embodiment, for the compounds of formula (Ia), $R^5$, $R^6$, $R^7$ and $R^{10}$ are each —H, $R^3$ is —$CH_3$, $R^4$ is —$NH_2$, and $R^8$ is —$OCH_3$.

In one embodiment, for the compounds of formula (Ia), $R^5$, $R^6$, $R^7$ and $R^{10}$ each —H, $R^3$ is —$C_1$-$C_6$ alkyl, $R^4$ is —OH, and $R^8$ is —O—$C_1$-$C_6$ alkyl.

In another embodiment, for the compounds of formula (Ia), $R^5$, $R^6$, $R^7$ and $R^{10}$ each —H, $R^3$ is —$C_1$-$C_6$ alkyl, $R^4$ is —$OCH_3$, and $R^8$ is —O—$C_1$-$C_6$ alkyl.

In still another embodiment, for the compounds of formula (Ia), $R^5$, $R^6$, $R^7$ and $R^{10}$ each —H, $R^3$ is —$C_1$-$C_6$ alkyl, $R^4$ is —$NH_2$, $R^8$ is —O—$C_1$-$C_6$ alkyl and $R^9$ is —O—$C_1$-$C_6$ alkyl.

In another embodiment, the compounds of formula (I) have the formula (Ib):

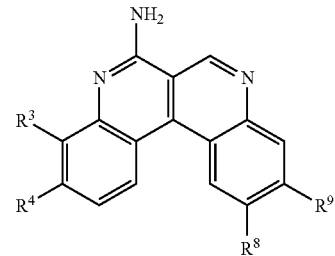

(Ib)

wherein $R^3$, $R^4$, $R^8$ and $R^9$ are as defined above for the compounds of formula (I).

Additional illustrative examples of the Dibenzonaphthyridine Derivatives of formula (I) include the compounds of Formula (Ib) as set forth below:

| Compound | $R^3$ | $R^4$ | $R^8$ | $R^9$ |
|---|---|---|---|---|
| Ib-1 | —H | —H | —$OCH_3$ | —$OCH_3$ |
| Ib-2 | —$CH_3$ | —$NH_2$ | —$OCH_3$ | —$OCH_3$ |
| Ib-3 | —$CH_3$ | —$NH_2$ | —OEt | —OEt |
| Ib-4 | —$CH_3$ | —$NH_2$ | —$OCH_3$ | —F |
| Ib-5 | —$CH_3$ | —$NH_2$ | —$OCH_3$ | —N($CH_3$)—($CH_2$)$_3$N($CH_3$)$_2$ |
| Ib-6 | —$CH_3$ | —$NH_2$ | —$OCH_3$ | —N($CH_3$)—($CH_2$)$_2$N($CH_3$)$_2$ |
| Ib-7 | —$CH_3$ | —$NH_2$ | —$OCH_3$ | —NH($CH_2$)$_3$-(1-methyl-piperazin-4-yl) |
| Ib-8 | —$CH_3$ | —$NH_2$ | —$OCH_3$ | —NH($CH_2$)$_3$-(morpholin-4-yl) |
| Ib-9 | —$CH_3$ | —$NH_2$ | —$OCH_3$ | —NH($CH_2$)$_2$-(morpholin-4-yl) |
| Ib-10 | —$CH_3$ | —$NH_2$ | —$OCH_3$ | —O—($CH_2$)$_2$-(morpholin-4-yl) |
| Ib-11 | —$CH_3$ | —$NH_2$ | —$OCH_3$ | —O—($CH_2$)$_3$-(morpholin-4-yl) |
| Ib-12 | —$CH_3$ | —$NH_2$ | —$OCH_3$ | —NH($CH_2$)$_3$-(pyrrolidin-1-yl) |
| Ib-13 | —$CH_3$ | —$NH_2$ | —$OCH_3$ | —NH($CH_2$)$_2$-(pyrrolidin-1-yl) |
| Ib-14 | —$CH_3$ | —$NH_2$ | —$OCH_3$ | —NH—($CH_2$)$_2$N($CH_3$)$_2$ |
| Ib-15 | —$CH_3$ | —$NH_2$ | —$OCH_3$ | —NH—($CH_2$)$_3$N($CH_3$)$_2$ |
| Ib-16 | —$CH_3$ | —$NH_2$ | —$OCH_3$ | —O—$CH_2$—(N-methyl-piperidin-4-yl) |
| Ib-17 | —$CH_3$ | —$NH_2$ | —O—($CH_2$)$_2$$OCH_3$ | —O—($CH_2$)$_2$$OCH_3$ |
| Ib-18 | —$CH_3$ | —$NH_2$ | —$OCH_3$ | —O—($CH_2$)$_2$Cl |
| Ib-19 | —$CH_3$ | —$NH_2$ | —$OCH_3$ | —O—($CH_2$)$_2$-(azindin-1-yl) |
| Ib-20 | —$CH_3$ | —$NH_2$ | —$OCH_3$ | —O($CH_2$)$_2$N($CH_3$)$_2$ |
| Ib-21 | —$CH_3$ | —$NH_2$ | —$OCH_3$ | —O($CH_2$)$_3$N($CH_3$)$_2$ |
| Ib-22 | —$CH_3$ | —$NH_2$ | —$OCH_3$ | —O—($CH_2$)$_2$-(pyrrolidin-1-yl) |
| Ib-23 | —$CH_3$ | —$NH_2$ | —$OCH_3$ | —O—($CH_2$)$_2$N(Et)$_2$ |
| Ib-24 | —$CH_3$ | —$NH_2$ | —$OCH_3$ | —O—($CH_2$)$_2$-(pyridin-2-yl) |
| Ib-25 | —$CH_3$ | —$NH_2$ | —$OCH_3$ | —O—($CH_2$)$_2$—(N-methyl-pyrrolidin-2-yl) |
| Ib-26 | —$CH_3$ | —$NH_2$ | —$OCH_3$ | —O—($CH_2$)$_2$-(piperidin-1-yl) |
| Ib-27 | —$CH_3$ | —$NH_2$ | —$OCH_3$ | —O—($CH_2$)$_3$N(Et)$_2$ |
| Ib-28 | —$CH_3$ | —$NH_2$ | —$OCH_3$ | —O—($CH_2$)$_2$-(azepan-1-yl) |
| Ib-29 | —$CH_3$ | —$NH_2$ | —$OCH_3$ | —O—($CH_2$)$_3$-(piperidin-1-yl) |
| Ib-30 | —$CH_3$ | —$NH_2$ | —$OCH_3$ | —O—($CH_2$)$_2$N($CH_3$)—($CH_2$)$_2$N($CH_3$)$_2$ |
| Ib-31 | —$CH_3$ | —$NH_2$ | —$OCH_3$ | —O—($CH_2$)$_2$-(indol-3-yl) |
| Ib-32 | —$CH_3$ | —$NH_2$ | —$OCH_3$ | —O—($CH_2$)$_2$-(4-(N,N-dimethylamino)-phenyl) |
| Ib-33 | —$CH_3$ | —$NH_2$ | —$OCH_3$ | —O—($CH_2$)$_2$-(N-methyl-piperidin-4-yl) |
| Ib-34 | —$CH_3$ | —$NH_2$ | —$OCH_3$ | —$OCH_2$—(N-methyl-piperidin-3-yl) |
| Ib-35 | —$CH_3$ | —$NH_2$ | —$OCH_3$ | —O—($CH_2$)$_3$-(pyrrolidin-1-yl-2-one) |
| Ib-36 | —$CH_3$ | -phthalimid-1-yl | —$OCH_3$ | —$OCH_3$ |
| Ib-37 | —$CH_3$ | —$NH_2$ | —$OCH_3$ | —OH |
| Ib-38 | —H | —$NH_2$ | —$OCH_3$ | —$OCH_3$ |
| Ib-39 | —$CH_3$ | —H | —$OCH_3$ | $OCH_3$ |
| Ib-40 | —$CH_3$ | —$NH_2$ | —$OCH_3$ | —O—($CH_2$)$_2$CH($CH_3$)$_2$ |
| Ib-41 | —$CH_3$ | —$NH_2$ | —$OCH_3$ | —O—($CH_2$)$_2$C($CH_3$)$_3$ |
| Ib-42 | —$CH_3$ | —$NH_2$ | —$OCH_3$ | —O—($CH_2$)$_3$—O-benzyl |

| Compound | R³ | R⁴ | R⁸ | R⁹ |
|---|---|---|---|---|
| Ib-43 | —CH₃ | —NH₂ | —OCH₃ | 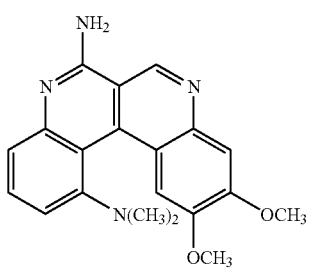 |
| Ib-44 | —CH₃ | —NH₂ | —OCH₃ | 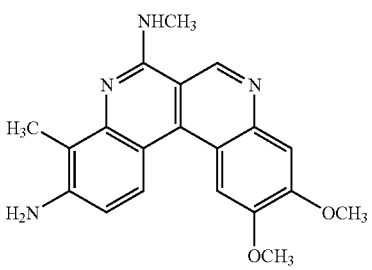 |
| Ib-45 | —CH₃ | —NH₂ | —OCH₃ | —O—(CH₂)₂-cyclopentyl |
| Ib-46 | —CH₃ | —NH₂ | —OCH₃ | —O—(CH₂)₂-cyclopropyl |
| Ib-47 | —CH₃ | —NH₂ | —OCH₃ | —O—(CH₂)₂—OEt |
| Ib-48 | —CH₃ | —NH₂ | —OCH₃ | —OH |
| Ib-49 | —CH₃ | —Cl | —OCH₃ | —OCH₃ |
| Ib-50 | —CH₃ | —OH | —OCH₃ | —OCH₃ |
| Ib-51 | —CH₃ | —OCH₃ | —OCH₃ | —OCH₃ |
| Ib-52 | —CH₃ | —NH₂ | —OCH₃ | —O—(CH₂)₂OCH₃ | and pharmaceutically acceptable salts thereof.

An additional illustrative Dibenzonaphthyridine Derivative of formula (Ib) is the compound set forth below:

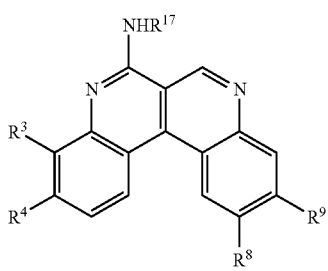

Ib-53 and pharmaceutically acceptable salts thereof.

In another embodiment, the compounds of formula (I) have the formula (Ic):

(Ic)

wherein R³, R⁴, R⁸, R⁹ and R¹⁷ are as defined above for the compounds of formula (I).

An additional illustrative example of a Dibenzonaphthyridine Derivative of formula (I) is the compound of Formula (Ic) as set forth below:

Ic-1 and pharmaceutically acceptable salts thereof.

Illustrative Dibenzonaphthyridine Derivatives may also be described using chemical nomenclature, as set forth below:

| Compound | Chemical Name |
|---|---|
| I-1 | 2,3,7,10-tetramethoxy-9-methyldibenzo[c,f]-2,7-naphthyridine |
| I-2 | 10,11-dimethoxy-4-methyldibenzo[c,f]-2,7-naphthyridine-3,6-diol |
| I-3 | 10,11-dimethoxy-4-methyldibenzo[c,f]-2,7-naphthyridin-3-amine |
| Ib-1 | 10,11-dimethoxydibenzo[c,f]-2,7-naphthyridin-6-amine |
| Ib-2 | 10,11-dimethoxy-4-methyldibenzo[c,f]-2,7-naphthyridine-3,6-diamine |
| Ib-3 | 10,11-diethoxy-4-methyldibenzo[c,f]-2,7-naphthyridine-3,6-diamine |
| Ib-4 | 10-fluoro-11-methoxy-4-methyldibenzo[c,f]-2,7-naphthyridine-3,6-diamine |
| Ib-5 | $N^{10}$-[3-(dimethylamino)propyl]-11-methoxy-$N^{10}$,4-dimethyldibenzo[c,f]-2,7-naphthyridine-3,6,10-triamine |
| Ib-6 | $N^{10}$-[2-(dimethylamino)ethyl]-11-methoxy-$N^{10}$,4-dimethyldibenzo[c,f]-2,7-naphthyridine-3,6,10-triamine |
| Ib-7 | 11-methoxy-4-methyl-$N^{10}$-[3-(4-methylpiperazin-1-yl)propyl]dibenzo[c,f]-2,7-naphthyridine-3,6,10-triamine |
| Ib-8 | 11-methoxy-4-methyl-$N^{10}$-(3-morpholin-4-ylpropyl)dibenzo[c,f]-2,7-naphthyridine-3,6,10-triamine |
| Ib-9 | 11-methoxy-4-methyl-$N^{10}$-(2-morpholin-4-ylethyl)dibenzo[c,f]-2,7-naphthyridine-3,6,10-triamine |
| Ib-10 | 11-methoxy-4-methyl-10-(2-morpholin-4-ylethoxy)dibenzo[c,f]-2,7-naphthyridine-3,6-diamine |
| Ib-11 | 11-methoxy-4-methyl-10-(3-morpholin-4-ylpropoxy)dibenzo[c,f]-2,7-naphthyridine-3,6-diamine |
| Ib-12 | 11-methoxy-4-methyl-$N^{10}$-(3-pyrrolidin-1-ylpropyl)dibenzo[c,f]-2,7-naphthyridine-3,6,10-triamine |
| Ib-13 | 11-methoxy-4-methyl-$N^{10}$-(2-pyrrolidin-1-ylethyl)dibenzo[c,f]-2,7-naphthyridine-3,6,10-triamine |
| Ib-14 | $N^{10}$-[2-(dimethylamino)ethyl]-11-methoxy-4-methyldibenzo[c,f]-2,7-naphthyridine-3,6,10-triamine |
| Ib-15 | $N^{10}$-[3-(dimethylamino)propyl]-11-methoxy-4-methyldibenzo[c,f]-2,7-naphthyridine-3,6,10-triamine |
| Ib-16 | 11-methoxy-4-methyl-10-[(1-methylpiperidin-4-yl)methoxy]dibenzo[c,f]-2,7-naphthyridine-3,6-diamine |
| Ib-17 | 10,11-bis(2-methoxyethoxy)-4-methyldibenzo[c,f]-2,7-naphthyridine-3,6-diamine |
| Ib-18 | 10-(2-chloroethoxy)-11-methoxy-4-methyldibenzo[c,f]-2,7-naphthyridine-3,6-diamine |
| Ib-19 | 10-(2-aziridin-1-ylethoxy)-11-methoxy-4-methyldibenzo[c,f]-2,7-naphthyridine-3,6-diamine |
| Ib-20 | 10-[2-(dimethylamino)ethoxy]-11-methoxy-4-methyldibenzo[c,f]-2,7-naphthyridine-3,6-diamine |
| Ib-21 | 10-[3-(dimethylamino)propoxy]-11-methoxy-4-methyldibenzo[c,f]-2,7-naphthyridine-3,6-diamine |
| Ib-22 | 11-methoxy-4-methyl-10-(2-pyrrolidin-1-ylethoxy)dibenzo[c,f]-2,7-naphthyridine-3,6-diamine |
| Ib-23 | 10-[2-(diethylamino)ethoxy]-11-methoxy-4-methyldibenzo[c,f]-2,7-naphthyridine-3,6-diamine |
| Ib-24 | 11-methoxy-4-methyl-10-(2-pyridin-2-ylethoxy)dibenzo[c,f]-2,7-naphthyridine-3,6-diamine |
| Ib-25 | 11-methoxy-4-methyl-10-[2-(1-methylpyrrolidin-2-yl)ethoxy]dibenzo[c,f]-2,7-naphthyridine-3,6-diamine |
| Ib-26 | 11-methoxy-4-methyl-10-(2-piperidin-1-ylethoxy)dibenzo[c,f]-2,7-naphthyridine-3,6-diamine |
| Ib-27 | 10-[3-(diethylamino)propoxy]-11-methoxy-4-methyldibenzo[c,f]-2,7-naphthyridine-3,6-diamine |
| Ib-28 | 10-(2-azepan-1-ylethoxy)-11-methoxy-4-methyldibenzo[c,f]-2,7-naphthyridine-3,6-diamine |
| Ib-29 | 11-methoxy-4-methyl-10-(3-piperidin-1-ylpropoxy)dibenzo[c,f]-2,7-naphthyridine-3,6-diamine |
| Ib-30 | 10-{2-[[2-(dimethylamino)ethyl](methyl)amino]ethoxy}-11-methoxy-4-methyldibenzo[c,f]-2,7-naphthyridine-3,6-diamine |
| Ib-31 | 10-[2-(1H-indol-3-yl)ethoxy]-11-methoxy-4-methyldibenzo[c,f]-2,7-naphthyridine-3,6-diamine |
| Ib-32 | 10-{2-[4-(dimethylamino)phenyl]ethoxy}-11-methoxy-4-methyldibenzo[c,f]-2,7-naphthyridine-3,6-diamine |
| Ib-33 | 11-methoxy-4-methyl-10-[2-(1-methylpiperidin-4-yl)ethoxy]dibenzo[c,f]-2,7-naphthyridine-3,6-diamine |
| Ib-34 | 11-methoxy-4-methyl-10-[(1-methylpiperidin-3-yl)methoxy]dibenzo[c,f]-2,7-naphthyridine-3,6-diamine |
| Ib-35 | 1-{3-[(7,10-diamino-2-methoxy-9-methyldibenzo[c,f]-2,7-naphthyridin-3-yl)oxy]propyl}pyrrolidin-2-one |
| Ib-36 | 2-(6-amino-10,11-dimethoxy-4-methyldibenzo[c,f]-2,7-naphthyridin-3-yl)-1H-isoindole-1,3(2H)-dione |
| Ib-37 | 10-amino-3-methoxy-9-methyldibenzo[c,f]-2,7-naphthyridin-2-ol |
| Ib-38 | 10,11-dimethoxydibenzo[c,f]-2,7-naphthyridine-3,6-diamine |
| Ib-39 | 10,11-dimethoxy-4-methyldibenzo[c,f]-2,7-naphthyridin-6-amine |
| Ib-40 | 11-methoxy-4-methyl-10-(3-methylbutoxy)dibenzo[c,f]-2,7-naphthyridine-3,6-diamine |

-continued

| Compound | Chemical Name |
|---|---|
| Ib-41 | 10-(3,3-dimethylbutoxy)-11-methoxy-4-methyldibenzo[c,f]-2,7-naphthyridine-3,6-diamine |
| Ib-42 | 10-[3-(benzyloxy)propoxy]-11-methoxy-4-methyldibenzo[c,f]-2,7-naphthyridine-3,6-diamine |
| Ib-43 | 10-{[(2S)-1-benzylpyrrolidin-2-yl]methoxy}-11-methoxy-4-methyldibenzo[c,f]-2,7-naphthyridine-3,6-diamine |
| Ib-44 | 11-methoxy-4-methyl-10-[((2S)-1-{[(2S)-1-methylpyrrolidin-2-yl]methyl}pyrrolidin-2-yl)methoxy]dibenzo[c,f]-2,7-naphthyridine-3,6-diamine |
| Ib-45 | 10-(2-cyclopentylethoxy)-11-methoxy-4-methyldibenzo[c,f]-2,7-naphthyridine-3,6-diamine |
| Ib-46 | 10-(2-cyclopropylethoxy)-11-methoxy-4-methyldibenzo[c,f]-2,7-naphthyridine-3,6-diamine |
| Ib-47 | 10-(2-ethoxyethoxy)-11-methoxy-4-methyldibenzo[c,f]-2,7-naphthyridine-3,6-diamine |
| Ib-48 | 7,10-diamino-2-methoxy-9-methyldibenzo[c,f]-2,7-naphthyridin-3-ol |
| Ib-49 | 3-chloro-10,11-dimethoxy-4-methyldibenzo[c,f]-2,7-naphthyridin-6-amine |
| Ib-50 | 6-amino-10,11-dimethoxy-4-methyldibenzo[c,f]-2,7-naphthyridin-3-ol |
| Ib-51 | 3,10,11-trimethoxy-4-methyldibenzo[c,f]-2,7-naphthyridin-6-amine |
| Ib-52 | 11-methoxy-10-(2-methoxyethoxy)-4-methyldibenzo[c,f]-2,7-naphthyridine-3,6-diamine |
| Ib-53 | 10,11-dimethoxy-$N^1$,$N^1$-dimethyldibenzo[c,f]-2,7-naphthyridine-1,6-diamine |
| Ic-1 | 10,11-dimethoxy-N-6,4-dimethyldibenzo[c,f]-2,7-naphthyridine-3,6-diamine | and pharmaceutically acceptable salts or hydrates thereof.

Another illustrative compound of Formula (I) is:

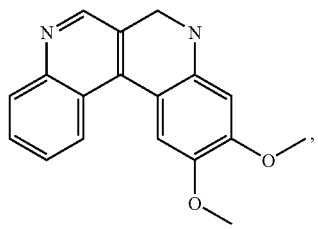

I-4

The compound of formula I-4 can alternatively be described as 2,3-dimethoxydibenzo[c,f]-2,7-naphthyridine.

4.3 Methods For Making The Dibenzonaphthyridine Derivatives

Examples of synthetic pathways that are useful for making Dibenzonaphthyridine Derivatives are set forth in the Examples below and generalized in Schemes 1-4.

Scheme 1 illustrates a method useful for making the Dibenzonaphthyridine Derivatives of formula (I) wherein $R^1$ is —NH$_2$, $R^2$ is —H, and $R^3$, $R^4$, $R^5$, $R^6$, $R^7$, $R^8$, $R^9$ and $R^{10}$ are as defined above for the compounds of formula (I).

Scheme 1

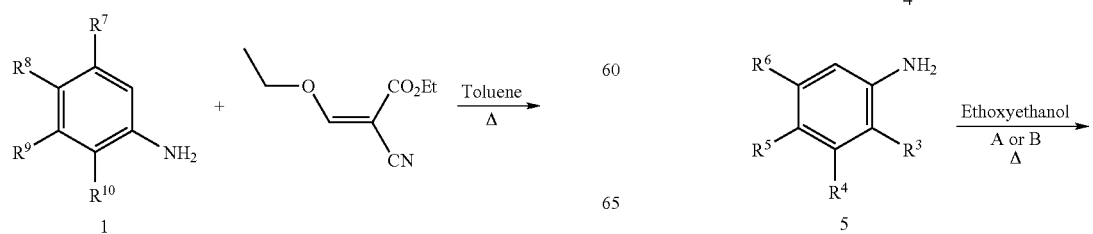

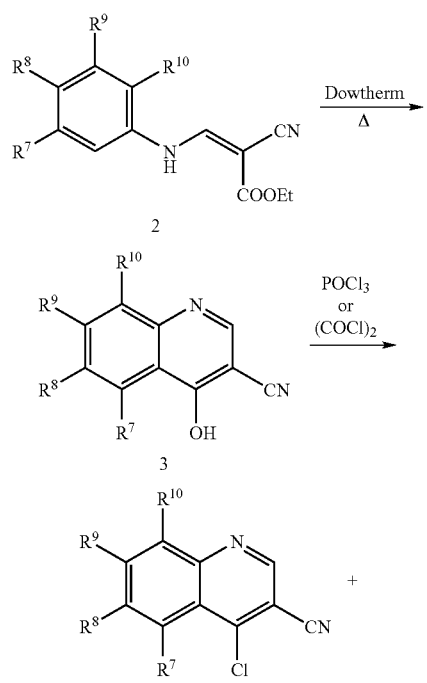

-continued

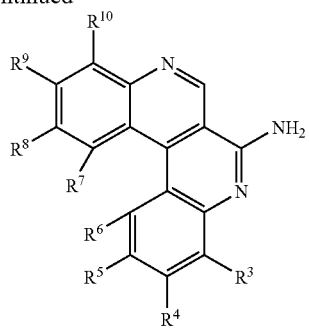

Dibenzonaphthyridine Derivatives of Formula (I), wherein $R^1$ is ——$NH_2$ and $R^2$ is——H wherein $R^3$, $R^4$, $R^5$, $R^6$, $R^7$, $R^8$, $R^9$ and $R^{10}$ are as defined above for the compounds of formula (I), $R^1$ is —$NH_2$ and $R^2$ is —H. A corresponds to Method A, which is described below, and B corresponds to Method B, which also is described below.

An aniline compound of formula 1 can be reacted with ethyl-(ethoxymethylene)-cyanoacetate to provide a nitrile compound of formula 2. A compound of formula 2 can then undergo a thermal cyclization to provide a substituted quinolinone compound of formula 3. The compound of formula 3 can then be chlorinated, for example using phosphorus oxychloride or oxalyl chloride, with or without heat, to provide a chloro compound of formula 4, which can further be reacted with an aniline compound of formula 5 with heating under non-microwave conditions (method A) or using microwave radiation (method B), in a high boiling point solvent such as ethoxyethanol, or neat, to provide compounds of formula (I) wherein $R^1$ is —$NH_2$ and $R^2$ is —H. The solvents and reagents, which include starting materials and intermediates, used in all schemes are intended to be illustrative.

In one embodiment, the invention provides methods for synthesizing compounds of Formula I, which include heating chemical reagents in high boiling solvents, optionally applying microwave radiation.

In one embodiment of method B, the reactions were carried out using microwave radiation with a power of less than 500 Watts and pressure of less than 40 psi. In another embodiment, the reactions were carried out using microwave radiation with a power of less than 300 Watts and pressure of less than 20 psi.

In one embodiment, high-boiling solvents are used in the synthesis of compounds of Formula (I). The intermediates may be dissolved or suspended in such solvents. The solvents may have a boiling point, at standard temperature and pressure, of 100° C. or higher, for example up to 200° C. or 300° C., such as nitrobenzene, ortho dichlorobenzene, diphenyl ether, polyethylene glycol, or ethyoxyethanol.

In one embodiment, method A and method B further include use of a proton catalyst, such as pyridine hydrochloride, para-toluene sulfonic acid, PPTS, a combination thereof, or the like.

Scheme 2 illustrates methods useful for making the compounds of formula (I), wherein one or more of $R^3$, $R^4$, $R^5$, $R^6$, $R^7$, $R^8$, $R^9$ and $R^{10}$ is —OH, —OY or —NHY, wherein Y is —$C_1$-$C_6$ alkyl, —$C_2$-$C_6$ alkenyl, —$C_2$-$C_6$ alkynyl or -phenyl.

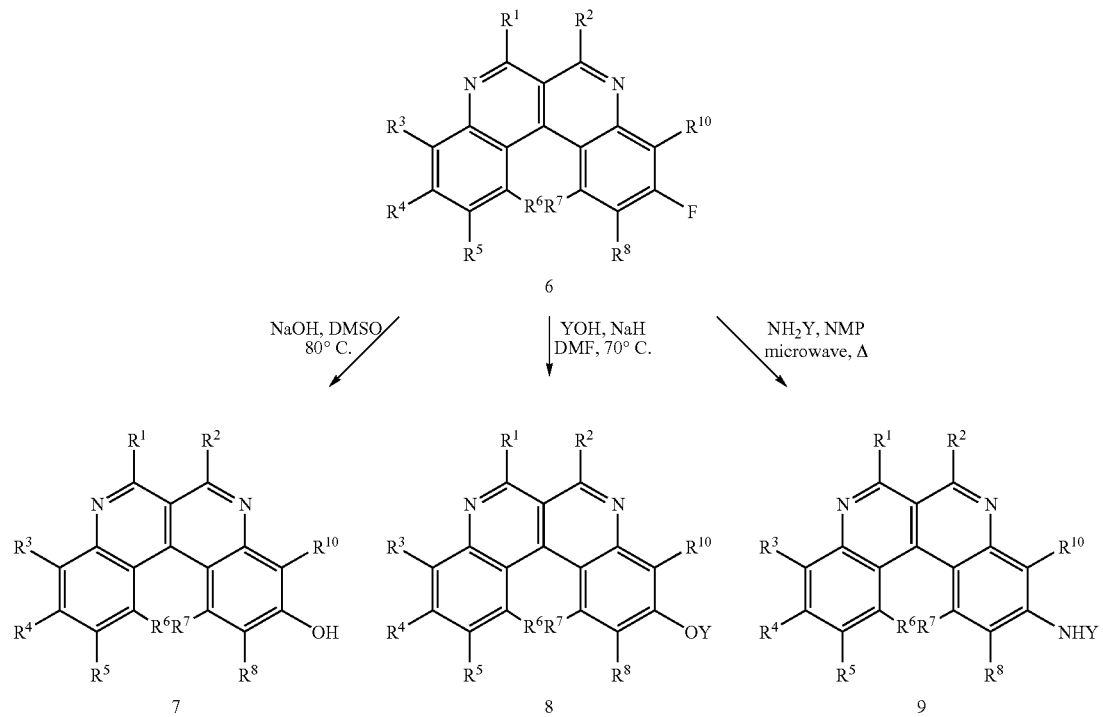

Scheme 2 wherein $R^1$, $R^2$, $R^3$, $R^4$, $R^5$, $R^6$, $R^7$, $R^8$ and $R^{10}$ are as defined above for the compounds of formula (I), and Y is —$C_1$-$C_6$ alkyl, —$C_2$-$C_6$ alkenyl, —$C_2$-$C_6$ alkynyl or -phenyl.

A fluoro-substituted compound of formula 6 can be reacted with: (i) NaOH in DMSO to provide the corresponding hydroxy-substituted compounds of formula 7; (ii) a compound of formula YOH in the presence of a suitable base, such as NaH, to provide the corresponding alkoxy-substituted compounds of formula 8; or (iii) a compound of formula $NH_2Y$ under microwave conditions in NMP to provide the corresponding amino-substituted compounds of formula 9. Although the methods described in Scheme 2 specifically illustrate chemical transformations at group $R^9$ of the Dibenzonaphthyridine Derivatives, it is to be understood that the methods described in Scheme 2 are general methods which are useful to make the Dibenzonaphthyridine Derivatives of formula (I) wherein one or more of any of the groups $R^3$, $R^4$, $R^5$, $R^6$, $R^7$, $R^8$, $R^9$ and $R^{10}$ may be substituted with an —OH, —OY or —NHY group, wherein Y is —$C_1$-$C_6$ alkyl, —$C_2$-$C_6$ alkenyl, —$C_2$-$C_6$ alkynyl or -phenyl.

In addition, a compound of formula 6 can be reacted: (i) with a compound of formula NaSH in the presence of a base to provide Dibenzonaphthyridine Derivatives of formula (I) wherein one or more of any of the groups $R^3$, $R^4$, $R^5$, $R^6$, $R^7$, $R^8$, $R^9$ and $R^{10}$ is substituted with an —SH, group, or (ii) with a compound of formula HSY in the presence of a base to provide Dibenzonaphthyridine Derivatives of formula (I) wherein one or more of any of the groups $R^3$, $R^4$, $R^5$, $R^6$, $R^7$, $R^8$, $R^9$ and $R^{10}$ is substituted with an —SY, group, wherein Y is —$C_1$-$C_6$ alkyl, —$C_2$-$C_6$ alkenyl, —$C_2$-$C_6$ alkynyl or -phenyl.

Scheme 3 illustrates a method useful for making the Dibenzonaphthyridine Derivatives of formula (I) wherein $R^1$ is —$NH_2$, $R^2$ is —H, and $R^3$, $R^4$, $R^5$, $R^6$, $R^7$, $R^8$, $R^9$ and $R^{10}$ are as defined above for the compounds of formula (I).

Scheme 3

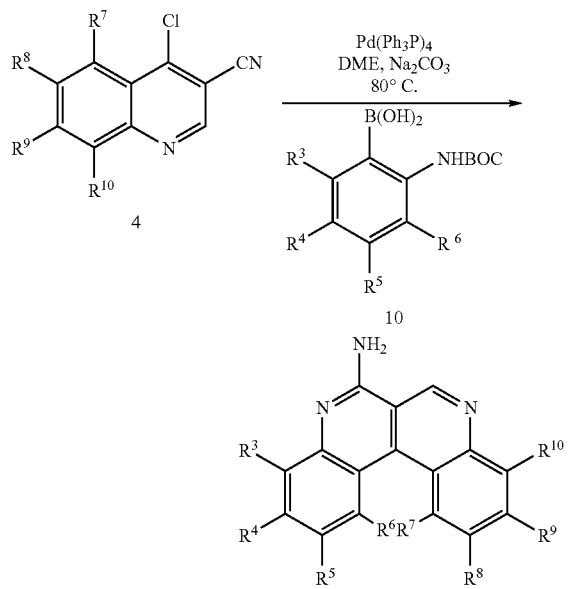

Dibenzonaphthyridine Derivatives of formula (I) whereine $R^1$ is —$NH_2$ and $R^2$ is —H.

wherein $R^3$, $R^4$, $R^5$, $R^6$, $R^7$, $R^8$, $R^9$ and $R^{10}$ are as defined above for the compounds of formula (I)

A nitrile compound of formula 4 can be cross-coupled with a phenyl boronic acid compound of formula 10 using Suzuki coupling conditions as described, for example, in Miyaura et al., *Chem. Rev.*, 95:2457 (1995), to provide the Dibenzonaphthyridine Derivatives of formula (I) wherein $R^1$ is —$NH_2$, $R^2$ is —H, and $R^3$, $R^4$, $R^5$, $R^6$, $R^7$, $R^8$, $R^9$ and $R^{10}$ are as defined above for the compounds of formula (I). Alternatively, cesium salts can be used instead of sodium carbonate, such as cesium carbonate or cesium fluoride.

Scheme 4 illustrates a method useful for making Dibenzonaphthyridine Derivative of formula (I), wherein one or more of $R^3$, $R^4$, $R^5$, $R^6$, $R^7$, $R^8$, $R^9$ and R10 is halo, —CN, —$SO_2Cl$, —$CH_3$, vinyl, or —C(O)—Y, and Y is —$C_1$-$C_6$ alkyl, —$C_2$-$C_6$ alkenyl, —$C_2$-$C_6$ alkynyl or phenyl.

Scheme 4

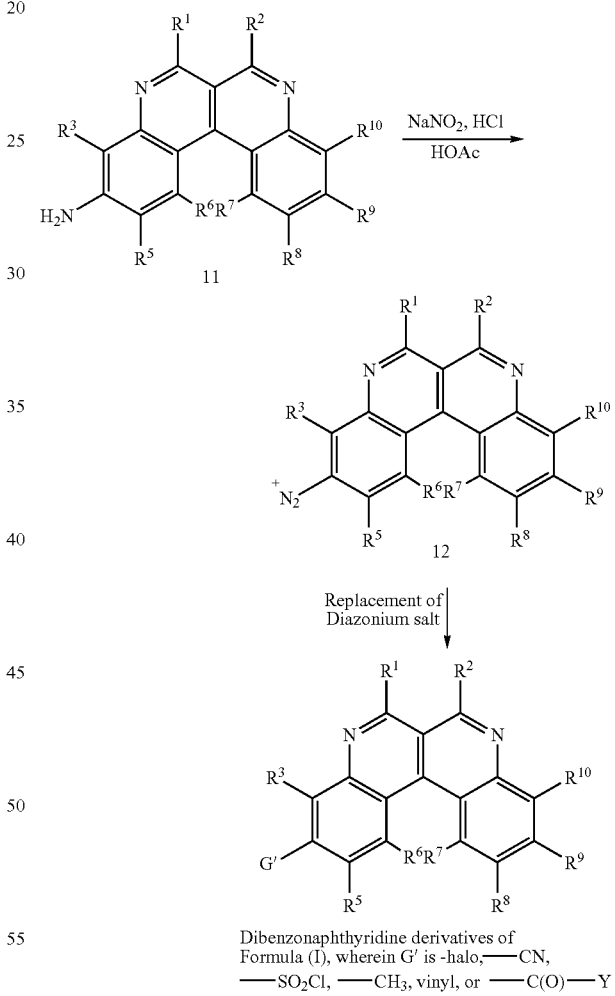

Dibenzonaphthyridine derivatives of Formula (I), wherein G' is -halo,—CN, —$SO_2Cl$, —$CH_3$, vinyl, or —C(O)—Y wherein $R^1$, $R^2$, $R^3$, $R^5$, $R^6$, $R^7$, $R^8$, $R^9$ and $R^{10}$ are as defined above for the compounds of formula (I), G' is halo, —CN, —$SO_2Cl$, —$CH_3$, vinyl, or —C(O)—Y, and Y is —$C_1$-$C_6$ alkyl, —$C_2$-$C_6$ alkenyl, —$C_2$-$C_6$ alkynyl or phenyl.

An amino-substituted compound of formula 11 (which can be prepared using the methods described in Scheme 1) can be diazotized using, for example, $NaNO_2$ to provide a diazo intermediate of formula 12. See March, *Advanced*

*Organic Chemistry: Reactions, Mechanisms and Structure*, Fourth Edition, John Wiley and Sons, p. 635-637 (1992). The diazonium salt of formula 12 can then be replaced with numerous functional groups as described in March, p. 723-725, to provide a Dibenzonaphthyridine Derivative of formula (I) wherein one or more of the groups $R^3$, $R^4$, $R^5$, $R^6$, $R^7$, $R^8$, $R^9$ and $R^{10}$ are substituted with -halo, —CN, —SO$_2$Cl, -methyl, -vinyl, or —C(O)(C$_1$-C$_6$ alkyl). Although the methods described in Scheme 2 specifically illustrate chemical transformations at group $R^4$ of the Dibenzonaphthyridine Derivatives, it is to be understood that the methods described in Scheme 4 are general methods which are useful to make the Dibenzonaphthyridine Derivatives of formula (I) wherein one or more of $R^3$, $R^4$, $R^5$, $R^6$, $R^7$, $R^8$, $R^9$ and $R^{10}$ is -halo, —CN, —SO$_2$Cl, —CH$_3$, vinyl, or —C(O)—Y, and Y is —C$_1$-C$_6$ alkyl, —C$_2$-C$_6$ alkenyl, —C$_2$-C$_6$ alkynyl or -phenyl.

The Compounds that can be made using the methods provided above in Schemes 1-4 can be derivatized using methods known to one skilled in the art of organic synthesis in order to provide the entire scope of the Dibenzonaphthyridine Derivatives of formula (I).

4.4 Methods For Using The Dibenzonaphthyridine Derivatives

In accordance with the invention, the Dibenzonaphthyridine Derivatives are administered to a subject in need of treatment or prevention of a proliferative disorder.

4.4.1 Methods for Treating or Preventing a Proliferative Disorder

A proliferative disorder can be treated or prevented by administration of an effective amount of a Dibenzonaphthyridine Derivative.

Proliferative disorders that can be treated or prevented by administering an effective amount of a Dibenzonaphthyridine Derivative include, but are not limited to, cancer, uterine fibroids, benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, an inflammatory bowel disease, transplantation rejection, endotoxic shock, a fungal infection, a defective apoptosis-associated condition, or a proliferative disease that is dependent on PDK-1 activity.

In one embodiment, the proliferative disorder is cancer.

In another embodiment, the proliferative disorder is a proliferative disorder that is dependent on PDK-1 activity.

4.4.2 Methods for Treating or Preventing Cancer

The Dibenzonaphthyridine Derivatives can be used to treat or prevent cancer.

The invention provides methods for treating or preventing cancer, comprising administering to a subject in need of such treatment or prevention an effective amount of a Dibenzonaphthyridine Derivative.

Examples of cancers treatable or preventable using the Dibenzonaphthyridine Derivatives include, but are not limited to, a cancer which expresses PDK-1, the cancers disclosed below in Table 1, and metastases thereof.

TABLE 1

| Solid tumors, including but not limited to: |
|---|
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon cancer |
| colorectal cancer |
| kidney cancer |
| pancreatic cancer |
| bone cancer |
| breast cancer |
| ovarian cancer |
| prostate cancer |
| esophageal cancer |
| stomach cancer |
| oral cancer |
| nasal cancer |
| throat cancer |
| squamous cell carcinoma |
| basal cell carcinoma |
| adenocarcinoma |
| sweat gland carcinoma |
| sebaceous gland carcinoma |
| papillary carcinoma |
| papillary adenocarcinomas |
| cystadenocarcinoma |
| medullary carcinoma |
| bronchogenic carcinoma |
| renal cell carcinoma |
| hepatoma |
| bile duct carcinoma |
| choriocarcinoma |
| seminoma |
| embryonal carcinoma |
| Wilms' tumor |
| cervical cancer |
| uterine cancer |
| testicular cancer |
| small cell lung carcinoma |
| bladder carcinoma |
| lung cancer |
| epithelial carcinoma |
| skin cancer |
| melanoma |
| neuroblastoma |
| retinoblastoma |
| Blood-borne cancers, including but not limited to: |
| acute lymphoblastic leukemia ("ALL") |
| acute lymphoblastic B-cell leukemia |
| acute lymphoblastic T-cell leukemia |
| acute myeloblastic leukemia ("AML") |
| acute promyelocytic leukemia ("APL") |
| acute monoblastic leukemia |
| acute erythroleukemic leukemia |
| acute megakaryoblastic leukemia |
| acute myelomonocytic leukemia |
| acute nonlymphocyctic leukemia |
| acute undifferentiated leukemia |
| chronic myelocytic leukemia ("CML") |
| chronic lymphocytic leukemia ("CLL") |
| hairy cell leukemia |
| multiple myeloma |

TABLE 1-continued

Lymphomas:

Hodgkin's disease
non-Hodgkin's Lymphomas:

Multiple myeloma
Waldenström's macroglobulinemia
Heavy chain disease
Polycythemia vera
CNS and brain cancers:

glioma
pilocytic astrocytoma
astrocytoma
anaplastic astrocytoma
glioblastoma multiforme
medulloblastoma
craniopharyngioma
ependymoma
pinealoma
hemangioblastoma
acoustic neuroma
oligodendroglioma
meningioma
vestibular schwannoma
adenoma
metastatic brain tumor
meningioma
spinal tumor
medulloblastoma In one embodiment the cancer is lung cancer, breast cancer, colorectal cancer, prostate cancer, a leukemia, a lymphoma, a skin cancer, a brain cancer, a cancer of the central nervous system, ovarian cancer, uterine cancer, stomach cancer, pancreatic cancer, esophageal cancer, kidney cancer, liver cancer, or a head and neck cancer.

In another embodiment the cancer is metastatic cancer.

In yet another embodiment the cancer is a cancer which expresses PDK-1.

In still another embodiment, the subject has previously undergone or is presently undergoing treatment for cancer. Such previous treatments include, but are not limited to, prior chemotherapy, radiation therapy, surgery or immunotherapy, such as cancer vaccines.

The Dibenzonaphthyridine Derivatives are also useful for the treatment or prevention of a cancer caused by a virus. Such viruses include human papilloma virus, which can lead to cervical cancer (see, e.g., Hemandez-Avila et al., Archives of Medical Research (1997) 28:265-271); Epstein-Barr virus (EBV), which can lead to lymphoma (see, e.g., Herrmann et al., J Pathol (2003) 199(2):140-5); hepatitis B or C virus, which can lead to liver carcinoma (see, e.g., El-Serag, J Clin Gastroenterol (2002) 35(5 Suppl 2):S72-8); human T cell leukemia virus (HTLV)-I, which can lead to T-cell leukemia (see e.g., Mortreux et al., Leukemia (2003) 17(1):26-38); human herpesvirus-8 infection, which can lead to Kaposi's sarcoma (see, e.g., Kadow et al., Curr Opin Investig Drugs (2002) 3(11):1574-9); and Human Immune deficiency Virus (HIV) infection, which can lead to cancer as a consequence of immunodeficiency (see, e.g., Dal Maso et al., Lancet Oncol (2003) 4(2):110-9).

The Dibenzonaphthyridine Derivatives can also be administered to prevent the progression of a cancer, including but not limited to the cancers listed in Table 1. Such prophylactic use includes that in which non-neoplastic cell growth consisting of hyperplasia, metaplasia, or most particularly, dysplasia has occurred.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the Dibenzonaphthyridine Derviatives. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are treatable or preventable according to the present methods.

In another embodiment, fibrocystic disease (cystic hyperplasia, mammary dysplasia, particularly adenosis (benign epithelial hyperplasia)) is treatable or preventable according to the present methods.

In other embodiments, a subject that exhibits one or more of the following predisposing factors for malignancy can be administered an amount of a Dibenzonaphthyridine Derivative which is effective to treat or prevent cancer: a chromosomal translocation associated with a malignancy (e.g., the Philadelphia chromosome for chronic myelogenous leukemia, t(14;18) for follicular lymphoma); familial polyposis or Gardner's syndrome; benign monoclonal gammopathy; a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; and exposure to carcinogens (e.g., smoking, second-hand smoke exposure, and inhalation of or contacting with certain chemicals).

5.3.2 Combination Chemotherapy For the Treatment of Cancer

In one embodiment, the present methods for treating cancer or preventing cancer further comprise administering another anticancer agent.

In one embodiment, the present invention provides methods for treating or preventing cancer in a subject, the method comprising the administration of an effective amount of: (i) a Dibenzonaphthyridine Derivative and (ii) another anticancer agent.

In one embodiment, (i) a Dibenzonaphthyridine Derivative and (ii) another anticancer agent are administered in doses commonly employed when such agents are used as monotherapy for the treatment of cancer.

In another embodiment, (i) a Dibenzonaphthyridine Derivative and (ii) another anticancer agent act synergistically and are administered in doses that are less than the doses commonly employed when such agents are used as monotherapy for the treatment of cancer.

The dosage of the (i) a Dibenzonaphthyridine Derivative, and (ii) another anticancer agent administered as well as the dosing schedule can depend on various parameters, including, but not limited to, the cancer being treated, the subject's general health, and the administering physician's discretion.

A Dibenzonaphthyridine Derivative can be administered prior to (e.g., 5 minutes, 15 minutes, 30 minutes, 45 minutes, 1 hour, 2 hours, 4 hours, 6 hours, 12 hours, 24 hours, 48 hour 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of another anticancer agent to a subject in need thereof. In various embodiments, i) a Dibenzonaphthyridine Derivative, and (ii) another anticancer agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart. In one embodiment, i) a Dibenzonaphthyridine Derivative, and (ii) another anticancer agent are administered within 3 hours of each other. In another embodiment, i) a Dibenzonaphthyridine Derivative, and (ii) another anticancer agent are administered 1 minute to 24 hours apart.

In one embodiment, an effective amount of a Dibenzonaphthyridine Derivative and an effective amount of another anticancer agent are present in the same composition. In one embodiment, this composition is useful for oral administration. In another embodiment, this composition is useful for intravenous administration.

Cancers that can be treated or prevented by administering a Dibenzonaphthyridine Derivative and another anticancer agent include, but are not limited to, the list of cancers set forth in Table 1.

In one embodiment the cancer is lung cancer, breast cancer, colorectal cancer, prostate cancer, a leukemia, a lymphoma, a skin cancer, a brain cancer, a cancer of the central nervous system, ovarian cancer, uterine cancer, stomach cancer, pancreatic cancer, esophageal cancer, kidney cancer, liver cancer, or a head and neck cancer.

The Dibenzonaphthyridine Derivative and the other anticancer agent can act additively or synergistically. A synergistic combination of a Dibenzonaphthyridine Derivative and another anticancer agent might allow the use of lower dosages of one or both of these agents and/or less frequent dosages of one or both of the Dibenzonaphthyridine Derivatives and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

In one embodiment, a Dibenzonaphthyridine Derivative and another anticancer agent act synergistically when administered in doses typically employed when such agents are used as monotherapy for the treatment of cancer. In another embodiment, a Dibenzonaphthyridine Derivative and another anticancer agent act synergistically when administered in doses that are less than doses typically employed when such agents are used as monotherapy for the treatment of cancer.

In one embodiment, the administration of an effective amount of a Dibenzonaphthyridine Derivative and an effective amount of another anticancer agent inhibits the resistance of a cancer to the Dibenzonaphthyridine Derivative and/or the other anticancer agent. In one embodiment, the cancer is a solid tumor.

In one embodiment, other anticancer agents useful in the methods and compositions of the present invention include, but are not limited to, a drug listed in Table 2 or a pharmaceutically acceptable salt thereof.

TABLE 2

| | |
|---|---|
| Alkylating agents | |
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| | Procarbazine |
| | Temozolomide |
| Platinum complexes: | Cisplatin |
| | Carboplatin |
| | Aroplatin |
| | Oxaliplatin |
| Plant Alkaloids | |
| Vinca alkaloids: | Vincristine |
| | Vinblastine |
| | Vindesine |
| | Vinorelbine |
| Taxanes: | Paclitaxel |
| | Docetaxel |
| DNA Topoisomerase Inhibitors | |
| Epipodophyllins: | Etoposide |
| | Teniposide |
| | Topotecan |
| | Irinotecan |
| | 9-aminocamptothecin |
| | Camptothecin |
| | Crisnatol |
| Mitomycins: | Mitomycin C |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonucleotide reductase Inhibitors: | Hydroxyurea |
| | Deferoxamine |
| Pyrimidine analogs: | |
| Uracil analogs: | 5-Fluorouracil |
| | Fluoxuridine |
| | Doxifluridine |
| | Ralitrexed |
| Cytosine analogs: | Cytarabine |
| | Cytosine arabinoside |
| | Fludarabine |
| | Gemcitabine |
| | Capecitabine |
| Purine analogs: | Mercaptopurine |
| | Thioguanine |
| | O-6-benzylguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |

TABLE 2-continued

| | |
|---|---|
| | beta-TGDR |
| | cyclocytidine |
| | guanazole |
| | inosine glycodialdehyde |
| | macebecin II |
| | Pyrazoloimidazole |
| Hormonal therapies: | |
| Receptor antagonists: | |
| Anti-estrogen: | Tamoxifen |
| | Raloxifene |
| | Megestrol |
| LHRH agonists: | Goserelin |
| | Leuprolide acetate |
| Anti-androgens: | Flutamide |
| | Bicalutamide |
| Retinoids/Deltoids | Cis-retinoic acid |
| Vitamin A derivative: | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A (2BA-2-DMHA) |
| Cytokines: | Interferon-α |
| | Interferon-β |
| | Interferon-γ |
| | Tumor necrosis factor |
| | Interleukin-2 |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Combretastatin A-4 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic gonadotropin (hCG) |
| | IM-862 |
| | Interleukins |
| | Kringle 5 (plasminogen fragment) |
| | Marimastat |
| | Metalloproteinase inhibitors |
| | 2-Methoxyestradiol |
| | MMI 270 (CGS 27023A) |
| | MoAb IMC-1C11 |
| | Neovastat |
| | NM-3 |
| | Panzem |
| | PI-88 |
| | Placental ribonuclease inhibitor |
| | Plasminogen activator inhibitor |
| | Platelet factor-4 (PF4) |
| | Prinomastat |
| | Prolactin 16 kD fragment |
| | Proliferin-related protein (PRP) |
| | PTK 787/ZK 222594 |
| | Retinoids |
| | Solimastat |
| | Squalamine |
| | SS 3304 |

TABLE 2-continued

| | |
|---|---|
| | SU 5416 |
| | SU6668 |
| | SU11248 |
| | Tetrahydrocortisol-S |
| | Tetrathiomolybdate |
| | Thalidomide |
| | Thrombospondin-1 (TSP-1) |
| | TNP-470 |
| | Transforming growth factor-beta (TGF-β) |
| | Vasculostatin |
| | Vasostatin (calreticulin fragment) |
| | ZD6126 |
| | ZD 6474 |
| | farnesyl transferase inhibitors (FTI) |
| | Bisphosphonates |
| Antimitotic agents: | Allocolchicine |
| | Halichondrin B |
| | Colchicine |
| | colchicine derivative |
| | dolastatin 10 |
| | Maytansine |
| | Rhizoxin |
| | Thiocolchicine |
| | trityl cysteine |
| Others: | |
| Isoprenylation inhibitors: | |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin |
| | Idarubicin |
| | Epirubicin |
| | Pirarubicin |
| | Zorubicin |
| | Mitoxantrone |
| MDR inhibitors: | Verapamil |
| $Ca^{2+}$ATPase inhibitors: | Thapsigargin |

Additional suitable other anticancer agents useful in the methods and compositions of the present invention include, but are not limited to abiraterone, acivicin, aclarubicin, acodazole, acronine, acylfulvene, adecypenol, adozelesin, aldesleukin, an ALL-TK antagonist, altretamine, ambamustine, ambomycin, ametantrone, amidox, amifostine, aminoglutethimide, aminolevulinic acid, amrubicin, amsacrine, anagrelide, anastrozole, andrographolide, an angiogenesis inhibitor, antarelix, anthramycin, an apoptosis gene modulator, apurinic acid, ara-CDP-DL-PTBA, arginine deaminase, L-asparaginase, asperlin, asulacrine, atamestane, atrimustine, axinastatin 1, axinastatin 2, axinastatin 3, azacitidine, azasetron, azatoxin, azetepa, azatyrosine, azotomycin, batimastat, benzodepa, bisantrene, bisnafide, bizelesin, brequinar, bropirimine, balanol, a BCR/ABL antagonist, beta-alethine, betaclamycin B, betulinic acid, bisaziridinylspermine, bisnafide, bistratene A, bizelesin, calcipotriol, calphostin C, calusterone, canarypox IL-2, carubicin, carboxyamidotriazole, CaRest M3, CARN 700, carzelesin, castanospermine, cecropin B, cetrorelix, chloroquinoxaline, cicaprost, cirolemycin, cladribine, clotrimazole, collismycin A, collismycin B, conagenin, crambescidin 816, crisnatol, cryptophycin 8, cryptophycin A derivatives, curacin A, cyclopentanthraquinones, cycloplatam, cypemycin, cytostatin, dacliximab, decitabine, dehydrodidemnin B, deslorelin, dexifosfamide, dexoirnaplatin, dexrazoxane, dexdiaziquone, didemnin B, didox, diethylnorspermine, dihydro-5-acytidine, dihydrotaxol, dioxamycin, diphenyl spiromustine, docosanol, dolasetron, droloxifene, dronabinol, duazomycin, duocarmycin SA, ecomustine, edatrexate, eflornithine, elsamitrucin, enloplatin, enpromate, epripridine, erbulozole, esorubicin, estramustine, estramustine, an estrogen antagonist, etanidazole, etoprine, exemestane, fadrozole, fazarabine, fenretinide, finasteride, flavopiridol, flezelastine, fluasterone, fluorodaunorunicin, floxuridine, flurocitabine, forfenimex, formestane, fostriecin, fotemustine, gadolinium texaphyrin, galocitabine, ganirelix, a gelatinase inhibitor, a glutathione inhibitor, hepsulfam, herbimycin A, heregulin, hexamethylene bisacetamide, hypericin, ibandronic acid, idoxifene, idramantone, ilmofosine, ilomastat, imatinib mesylate, imidazoacridones, imiquimod, an IGF-1 inhibitor, iobenguane, iodoipomeanol, iproplatin, irsogladine, isobengazole, isohomohalicondrin B, itasetron, jasplakinolide, leucovorin, levamisole, leuprorelin, liarozole, lissoclinamide 7, lobaplatin, lombricine, lometrexol, lonidamine, losoxantrone, lovastatin, loxoribine, lurtotecan, lutetium texaphyrin, lysofylline, mannostatin A, masoprocol, maspin, a matrix metalloproteinase inhibitor, mechlorethamine, megestrol acetate melphalan, metoclopramide, mifepristone, miltefosine, mirimostim, mitoguazone, mitolactol, mitonafide, mofarotene, molgramostim, mopidamol, a multiple drug resistance gene inhibitor, myriaporone, N-acetyldinaline, nafarelin, nagrestip, napavin, naphterpin, nartograstim, nedaplatin, nemorubicin, neridronic acid, nilutamide, nisamycin, a nitrogen mustard, a nitric oxide modulator, a nitrosourea, nitrullyn, nocodazole, octreotide, okicenone, onapristone, oracin, ormaplatin, osaterone, oxaunomycin, palauamine, palmitoylpamidronic acid, panaxytriol, panomifene, parabactin, pazelliptine, pegaspargase, peldesine, peliomycin, pentamustine, pentosan, pentostatin, pentrozole, peplomycin, perfosfamide, perflubron, perfosfamide, phenazinomycin, a phosphatase inhibitor, picibanil, pilocarpine, pipobroman, piposulfan, piritrexim, placetin A, placetin B, plicamycin, porfiromycin, plomestane, porfimer sodium, porfiromycin, prednimustine, prednisone, prostaglandin J2, microalgal, puromycin, pyrazoloacridine, pyrazofurin, a raf antagonist, raltitrexed, ramosetron, a ras famesyl protein transferase inhibitor, a ras-GAP inhibitor, retelliptine demethylated, RII retinamide, riboprine, rogletimide, rohitukine, romurtide, roquinimex, rubiginone B1, ruboxyl, safingol, saintopin, SarCNU, sarcophytol A, sargramostim, semustine, a signal transduction modulator, simtrazene, sizofiran, sobuzoxane, solverol, sonermin, sparfosic acid, sparfosate, sparsomycin, spicamycin D, spiromustine, spiroplatin, splenopentin, spongistatin 1, a stem-cell division inhibitor, stipiamide, streptonigrin, a stromelysin inhibitor, sulfinosine, suradista, suramin, swainsonine, talisomycin, tallimustine, tauromustine, tazarotene, tecogalan, tegafur, tellurapyrylium, a telomerase inhibitor, teloxantrone, temoporfin, teroxirone, testolactone, tetrachlorodecaoxide, tetrazomine, thaliblastine, thiamiprine, thiocoraline, thrombopoietin, thymalfasin, thymotrinan, tirapazamine, titanocene, topsentin, toremifene, trestolone, tretinoin, triacetyluridine, triciribine, trimetrexate, triptorelin, tropisetron, tubulozole, turosteride, a tyrosine kinase inhibitor, ubenimex, uracil mustard, uredepa, vapreotide, variolin B, velaresol, veramine, verteporfin, vinxaltine, vinepidine, vinglycinate, vinleurosine, vinrosidine, vinzolidine, vitaxin, vorozole, zanoterone, zeniplatin, zilascorb, zinostatin, and zorubicin.

In various embodiments, the other anticancer agent is an alkylating agent, a platinum-containing agent, an anthracycline, a vinca alkaloid, a taxane, a topoisomerase inhibitor or an angiogenesis inhbitor.

In one embodiment, the other anticancer agent is administered orally.

In another embodiment, the other anticancer agent is administered intravenously.

5.3.3 Multi-Therapy For Cancer

The Dibenzonaphthyridine Derivatives can be administered to a subject that has undergone or is currently undergoing one or more additional anticancer therapies including, but not limited to, surgery, radiation therapy, or immunotherapy, such as cancer vaccines.

In one embodiment, the invention provides methods for treating or preventing cancer comprising administering to a subject in need thereof (a) an amount of a Dibenzonaphthyridine Derivative effective to treat or prevent cancer; and (b) another anticancer therapy including, but not limited to, surgery, radiation therapy, or immunotherapy, such as a cancer vaccine.

In one embodiment, the other anticancer therapy is radiation therapy.

In another embodiment, the other anticancer therapy is surgery.

In still another embodiment, the other anticancer therapy is immunotherapy.

In a specific embodiment, the present methods for treating or preventing cancer comprise administering a Dibenzonaphthyridine Derivative and radiation therapy. The radiation therapy can be administered concurrently with, prior to, or subsequent to the Dibenzonaphthyridine Derivative, in one embodiment, at least an hour, five hours, 12 hours, a day, a week, a month, or several months (e.g., up to three months), prior or subsequent to administration of the Dibenzonaphthyridine Derivatives.

Where the other anticancer therapy is radiation therapy, any radiation therapy protocol can be used depending upon the type of cancer to be treated. For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered.

Additionally, in one embodiment the invention provides methods of treatment of cancer using a Dibenzonaphthyridine Derivative as an alternative to chemotherapy or radiation therapy where the chemotherapy or the radiation therapy results in negative side effects in the subject being treated. The subject being treated can, optionally, be treated with another anticancer therapy such as surgery, radiation therapy, or immunotherapy.

The Dibenzonaphthyridine Derivatives can also be used in vitro or ex vivo, such as for the treatment of certain cancers, including, but not limited to leukemias and lymphomas, wherein such treatment involves autologous stem cell transplants. This can involve a process in which the subject's autologous hematopoietic stem cells are harvested and purged of all cancer cells, the subject's remaining bone-marrow cell population is then eradicated via the administration of a Dibenzonaphthyridine Derivative and/or radiation, and the resultant stem cells are infused back into the subject. Supportive care can be subsequently provided while bone marrow function is restored and the subject recovers.

4.5 Therapeutic/Prophylactic Administration

In one embodiment, the invention provides compositions useful for treating or preventing a proliferative disorder. The compositions are suitable for internal use and comprise an effective amount of a Dibenzonaphthyridine Derivative and a physiologically acceptable carrier or vehicle.

The Dibenzonaphthyridine Derivatives can be administered in amounts that are effective to treat or prevent a proliferative disorder in a subject.

Administration of the Dibenzonaphthyridine Derivatives can be accomplished via any mode of administration for therapeutic agents. These modes include systemic or local administration such as oral, nasal, parenteral, transdermal, subcutaneous, vaginal, buccal, rectal or topical administration modes. In some instances, administration will result in the release of a Dibenzonaphthyridine Derivative into the bloodstream.

In one embodiment, the Dibenzonaphthyridine Derivatives are administered orally.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids; suspensions, or the like, preferably in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions include tablets and gelatin capsules comprising a Dibenzonaphthyridine Derivative and a physiologically acceptable carrier or vehicle. Illustrative carriers or vehicles include a) a diluent, e.g., lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; and/or e) absorbent, colorant, flavorant and sweetener.

Liquid, particularly injectable, compositions can, for example, be prepared by dissolution, dispersion, etc. For example, the Dibenzonaphthyridine Derivative is dissolved in or mixed with a pharmaceutically acceptable solvent such as, for example, water, saline, aqueous dextrose, glycerol, ethanol, and the like, to thereby form an injectable isotonic solution or suspension.

The Dibenzonaphthyridine Derivatives can be also formulated as a suppository that can be prepared from fatty emulsions or suspensions; using polyalkylene glycols such as propylene glycol, as the carrier.

The Dibenzonaphthyridine Derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Dibenzonaphthyridine Derivatives can also be delivered by the use of monoclonal antibodies as individual carriers to which the Dibenzonaphthyridine Derivative molecules are coupled. The Dibenzonaphthyridine Derivatives can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the Dibenzonaphthyridine Derivatives can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Parental injectable administration can be used for subcutaneous, intramuscular or intravenous injections and infusions. Injectables can be prepared in conventional forms, either as liquid solutions or suspensions or solid forms suitable for dissolving in liquid prior to injection.

One embodiment, for parenteral administration employs the implantation of a slow-release or sustained-released system, according to U.S. Pat. No. 3,710,795, incorporated herein by reference.

The compositions can be sterilized or contain non-toxic amounts of adjuvants, such as preserving, stabilizing, wetting or emulsifying agents, solution promoters, salts for regulating the osmotic pressure pH buffering agents, and other substances, including, but not limited to, sodium acetate or triethanolamine oleate. In addition, they can also contain other therapeutically valuable substances.

Compositions can be prepared according to conventional mixing, granulating or coating methods, respectively, and the present pharmaceutical compositions can contain from about 0.1% to about 99%, preferably from about 1% to about 70% of the Dibenzonaphthyridine Derivative by weight or volume.

The dosage regimen utilizing the Dibenzonaphthyridine Derivative can be selected in accordance with a variety of factors including type, species, age, weight, sex and medical condition of the subject; the severity of the condition to be treated; the route of administration; the renal or hepatic function of the subject; and the particular Dibenzonaphthyridine Derivative employed. A person skilled in the art can readily determine and prescribe the effective amount of the drug useful for treating or preventing a proliferative disorder.

Effective dosage amounts of the Dibenzonaphthyridine Derivatives, when administered to a subject, range from about 0.05 to about 1000 mg of Dibenzonaphthyridine Derivative per day. Compositions for in vivo or in vitro use can contain about 0.5, 1.0, 2.5, 5.0, 10.0, 15.0, 25.0, 50.0, 100.0, 250.0, 500.0 or 1000.0 mg of Dibenzonaphthyridine Derivative. In one embodiment, the compositions are in the form of a tablet that can be scored. Effective plasma levels of the Dibenzonaphthyridine Derivatives can range from about 0.002 mg to about 50 mg per kg of body weight per day. The amount of a Dibenzonaphthyridine Derivative that is effective in the treatment or prevention of cancer can be determined by clinical techniques that are known to those of skill in the art. In addition, in vitro and in vivo assays can optionally be employed to help identify optimal dosage ranges. The precise dose to be employed can also depend on the route of administration, and the seriousness of the proliferative disorder being treated and can be decided according to the judgment of the practitioner and each subject's circumstances in view of, e.g., published clinical studies. Suitable-effective dosage amounts, however, can range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one Dibenzonaphthyridine Derivative is administered, the effective dosage amounts correspond to the total amount administered.

The dosage regimen utilizing the Dibenzonaphthyridine Derivative can be selected in accordance with a variety of factors including type, species, age, weight, sex and medical condition of the subject; the severity of the proliferative disorder to be treated; the route of administration; the renal or hepatic function of the subject; and the particular Dibenzonaphthyridine Derivative employed. A person skilled in the art can readily determine and prescribe the effective amount of the drug required to prevent, counter or arrest the progress of the proliferative disorder.

Dibenzonaphthyridine Derivatives can be administered in a single daily dose, or the total daily dosage can be administered in divided doses of two, three or four times daily. Furthermore, Dibenzonaphthyridine Derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of Dibenzonaphthyridine Derivative ranges from about 0.1% to about 15%, w/w or w/v.

In one embodiment, the compositions comprise an amount of each of a Dibenzonaphthyridine Derivative and another anticancer agent which together are effective to treat or prevent cancer. In another embodiment, the amount of Dibenzonaphthyridine Derivative and another anticancer agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of a Dibenzonaphthyridine Derivative and another anticancer agent. Other compositions of the present invention are prepared so that a parenteral dosage unit contains from about 0.01% to about 2% by weight of the composition.

The Dibenzonaphthyridine Derivatives can be assayed in vitro or in vivo for the desired therapeutic or prophylactic activity prior to use in humans. Animal model systems can be used to demonstrate safety and efficacy.

The present methods for treating or preventing cancer in a subject in need thereof can further comprise administering another prophylactic or therapeutic agent to the subject being administered a Dibenzonaphthyridine Derivative. In one embodiment the other prophylactic or therapeutic agent is administered in an effective amount. The other prophylactic or therapeutic agent includes, but is not limited to, an anti-inflammatory agent, an anti-renal failure agent, an anti-diabetic agent, and anti-cardiovascular disease agent, an antiemetic agent, a hematopoietic colony stimulating factor, an anxiolytic agent, and an analgesic agent.

In a further embodiment, the Dibenzonaphthyridine Derivative can be administered prior to, concurrently with, or after an antiemetic agent, or on the same day, or within 1 hour, 2 hours, 12 hours, 24 hours, 48 hours or 72 hours of each other.

In another embodiment, the Dibenzonaphthyridine Derivative can be administered prior to, concurrently with, or after a hematopoietic colony stimulating factor, or on the same day, or within 1 hour, 2 hours, 12 hours, 24 hours, 48 hours, 72 hours, 1 week, 2 weeks, 3 weeks or 4 weeks of each other.

In still embodiment, the Dibenzonaphthyridine Derivative can be administered prior to, concurrently with, or after an opioid or non-opioid analgesic agent, or on the same day, or within 1 hour, 2 hours, 12 hours, 24 hours, 48 hours or 72 hours of each other.

In yet another embodiment, the Dibenzonaphthyridine Derivative can be administered prior to, concurrently with, or after an anxiolytic agent, or on the same day, or within 1 hour, 2 hours, 12 hours, 24 hours, 48 hours or 72 hours of each other.

Effective amounts of the other therapeutic agents are well known to those skilled in the art. However, it is well within the skilled artisan's purview to determine the other therapeutic agent's optimal effective amount range. In one embodiment of the invention, where, another therapeutic agent is administered to a subject, the effective amount of the Dibenzonaphthyridine Derivative is less than its effective amount would be where the other therapeutic agent is not administered. In this case, without being bound by theory, it is believed that the Dibenzonaphthyridine Derivative and the other therapeutic agent act synergistically to treat or prevent cancer.

Antiemetic agents useful in the methods of the present invention include include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, and tropisetron.

Hematopoietic colony stimulating factors useful in the methods of the present invention include, but are not limited to, filgrastim, sargramostim, molgramostim and epoietin alfa.

Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

Non-opioid analgesic agents useful in the methods of the present invention include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

4.6 Kits

The invention encompasses kits that can simplify the administration of a Dibenzonaphthyridine Derivative to a subject.

A typical kit of the invention comprises a unit dosage form of a Dibenzonaphthyridine Derivative. In one embodiment the unit dosage form is a container, which can be sterile, containing an effective amount of a Dibenzonaphthyridine Derivative and a physiologically acceptable carrier or vehicle. The kit can further comprise a label or printed instructions instructing the use of the Dibenzonaphthyridine Derivative to treat or prevent cancer. The kit can also further comprise a unit dosage form of another prophylactic or therapeutic agent, for example, a container containing an effective amount of another prophylactic or therapeutic agent or another anticancer agent. In one embodiment the kit comprises a container containing an effective amount of a Dibenzonaphthyridine Derivative-and an effective amount of another prophylactic or therapeutic agent. Examples of other prophylactic or therapeutic agents and other anticancer agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag. The invention is further described in the following examples, which do not limit the scope of the invention described in the claims.

The following examples illustrate the synthesis of illustrative Dibenzonaphthyridine Derivatives and demonstrate their usefulness for treating or preventing a proliferative disorder.

5. EXAMPLES

General Methods

Selected synthetic intermediates and illustrative Dibenzonaphthyridine Derivatives were characterized on the basis of melting point, $^1$H NMR and/or MS data. $^1$H NMR spectra were obtained using a Bruker AM-400 (400 MHz) spectrophotometer and chemical shift values ($\delta$) are reported in parts per million (ppm). Mass spectrometry data was obtained using an Agilent MSD LC/MS instrument employing an API-ES ionization mode. Unless otherwise indicated, all HPLC purification procedures referred to in the Examples below were performed using an Agilent MSD LC/MS instrument fitted with an Aquasil C18 reverse-phase column (column temperature 40° C.), eluted at a flow rate of 0.800 mL/min using the following gradient of a mobile phase consisting of a mixture of 0.1% Formic Acid in water (by volume) and 0.1% Formic Acid in acetonitrile (by volume).

Gradient Table:

| Time (min) | % formic acid in acetonitrile |
|---|---|
| 0 | 0 |
| 2.5 | 100 |
| 4.0 | 100 |
| 4.1 | 0 |
| 5.5 | 0 |

Column output was monitored using UV detection at 215 nm, 230 nm, 254 nm, 280 nm, and 300 nm. HPLC retention times for illustrative Dibenzonaphthyridine Derivatives were also calculated using this procedure and the purity of illustrative compounds was determined at 254 nm.

Example 1

Synthesis of Compound Ib-38

Step A: Preparation of 2-cyano-3-(3,4-dimethoxyphenylamino)acrylic acid ethyl ester 3,4-dimethoxyaniline (30.6 g, 200 mmol) was diluted with toluene (80 mL) and to the resultant solution was added ethyl(ethoxymethylene)cyanoacetate (33.8 g, 200 mmol). The resultant reaction was heated to 100° C. and allowed to stir at for 1 hour, then heated to 125° C. and allowed to stir for 15 minutes. The reaction mixture was cooled to room temperature and concentrated in vacuo to provide a crude residue, which was recrystallized from EtOAc to provide 2-cyano-3-(3,4-dimethoxyphenylamino)acrylic acid ethyl ester as a tan solid (40.0 g, 72%). mp 166-170° C.; MS (ES+) m/z 277.2 [M+H].

Step B: Preparation of 6,7-dimethoxy-4-oxo-1,4-dihydroquinoline-3-carbonitrile

A mixture of 2-cyano-3-(3,4-dimethoxyphenylamino) acrylic acid ethyl ester (from Step A, 40 g, 145 mmol) and Dowtherm A (1.2 L) was heated to reflux and allowed to stir under nitrogen atmosphere for 10 hours. The resultant reaction mixture was then allowed to cool to 50° C. and diluted with hexane. The resultant suspension was filtered and the collected solid was sequentially washed with hexane and methylene chloride, then dried in vacuo to provide 6,7-dimethoxy-4-oxo-1,4-dihydroquinoline-3-carbonitrile as a brown solid (21.1 g, 63%). mp 330-350° C. dec; $^1$H NMR (DMSO-d6)$\delta$ 12.57 (s,1H), 8.59 (s, 1H), 7.44 (s, 1H), 7.03 (s, 1H), 3.89 (s, 3H), 3.87 (s, 3H); MS (ES+) m/z 231.0 [M+H].

Step C: Preparation of 4-chloro-6,7-dimethoxyquinoline-3-carbonitrile

A mixture of 6,7-dimethoxy-4-oxo-1,4-dihydroquinoline-3-carbonitrile (from Step B, 20 g, 87 mmol) and POCl$_3$ (87 mL) was heated to reflux and allowed to stir for 2 hours. The reaction mixture was cooled to 70° C. and concentrated in vacuo to provide a crude residue. The crude residue was diluted with methylene chloride and the resultant solution was cooled to 0° C. and to the resultant solution was added aqueous $K_2CO_3$ until the solution was at pH 8-9. The resultant solution was allowed to stir for 30 minutes at 25° C., then transferred to a separatory funnel. The organic layer was collected, washed with water, dried over sodium sulfate, filtered through celite, and concentrated in vacuo to provide 4-chloro-6,7-dimethoxyquinoline-3-carbonitrile as an off-white solid (19.8 g, 92%). A sample recrystallized from methylene chloride was characterized as follows: mp 220-223° C.; $^1$H NMR (DMSO-d6)δ 8.98 (s, 1H), 7.54 (s, 1H), 7.42 (s, 1H), 4.02 (s, 3H), 4.01 (s, 3H).

Step D: Preparation of Compound !b-38 (using Method A):

A mixture of 4-chloro-6,7-dimethoxyquinoline-3-carbonitrile (from Step C, 2.5 g, 10 mmol), 1,3-diaminobenzene (2.4 g, 20 mmol), and 2-ethoxyethanol (50 mL) was heated to reflux and allowed to stir for about 15 hours. The resultant reaction mixture was concentrated in vacuo to provide a crude residue, which was diluted with ethyl acetate (300 mL) and the resultant solution was transferred to a separatory funnel. The organic layer was collected and sequentially washed with saturated sodium bicarbonate (200 mL) and brine (200 mL). The organic layer was then collected, dried over sodium sulfate, filtered, then concentrated in vacuo to provide a crude residue. The crude residue was purified using flash column chromatography (120 g silica gel column, eluted with 12.5% 0.2 N ammonia in methanol/methylene chloride) to provide Compound Ib-38 as a yellow solid (2.6 g, 79% yield). MS 335 [M+H]; MS (ES+) m/z 335.1 [M+H]; $^1$H NMR (DMSO-d6): δ 9.4 (1H, s); 8.4 (1H, d); 8.2 (1H, s); 7.5 (1H, s); 6.9 (1H, br); 6.8 (1H, d); 5.4 (2H, br); 4.0 (3H, s); 3.9 (1H, s); 2.4 (3H, s), HPLC: Rt=2.08 minutes.

Example 2

Synthesis of Compound Ib-2

Using Method A
A stirred mixture of 4-chloro-6,7-dimethoxyquinoline-3-carbonitrile (25 mg, 0.10 mmol), 2,6-diaminotoluene (49 mg, 0.40, mmol) and pyridine hydrochloride (58 mg, 0.50 mmol) in 2 mL of 2-ethoxyethanol was heated at 130° for 8 h. 10,11-dimethoxy-4-methyldibenzo[c,f]-2,7-naphthyridine-3,6-diamine Ib-2 was formed in 65% yield based on the LC/MS intergation.

Using Method B
A stirred mixture of 4-chloro-6,7-dimethoxyquinoline-3-carbonitrile (25 mg, 0.10 mmol), 2,6-diaminotoluene (24 mg, 0.20 mmol) and pyridine hydrochloride (12 mg, 0.10 mmol) in 2 mL of 2-ethoxyethanol was heated at 210° in a microwave oven for 1 h using a power limit of 300 Watts and a pressure inside the reaction vessel of less than 20 psi. 10,11-dimethoxy-4-methyldibenzo[c,f]-2,7-naphthyridine-3,6-diamine Ib-2 was formed in 80% yield based on LC/MS intergation. The reaction mixture was concentrated in vacuo to provide a crude residue, which was diluted with ethyl acetate and the resultant solution transferred to a separatory funnel. The organic layer was collected and sequentially washed with saturated sodium bicarbonate and brine. The organic layer was then collected, dried over sodium sulfate, filtered, then concentrated in vacuo to provide a crude residue. The crude residue was purified using flash column chromatography using a gradient from 5% to 10% of 0.2N ammonia in methanol/methylene chloride. Isolated yield: 72%. Compound Ib-2: HPLC: Rt=2.13 min; MS (ES+) m/z 335.1; [M+H]. HRMS: 335.15122 [M+H]; 335.15026 [calculated]; $^1$H NMR (DMSO-d6): δ 9.4 (1H, s); 8.4 (1H, d); 8.2 (1H, s); 7.5 (1H, s); 6.9 (1H, br); 6.8 (1H, d); 5.4 (2H, br); 4.0 (3H, s); 3.9 (1H, s); 2.4 (3H, s); IR (cm$^{-1}$). The cyano group's absorption at approximately 2200 cm$^{-1}$ is not observed.

Example 3

Synthesis of Compounds Ib-3, Ib-4, Ib-17, Ib-18 and Ib-53

Using the procedure described in Example 1 and substituting 3,4-diethoxyaniline for 3,4-dimethoxyaniline in Step A, and 2,6-diaminotoluene for 1,3-diaminobenzene in Step C, Compound Ib-3 was prepared. MS 363 [M+H], HPLC: Rt=2.40 minutes Using the procedure described in Example 1 and substituting 3-fluoro-4-methoxyaniline for 3,4-dimethoxyaniline in Step A, and 2,6-diaminotoluene for 1,3-diaminobenzene in Step C, Compound Ib-4 was prepared. MS 323 [M+H], HPLC: Rt=1.75 minutes Using the procedure described in Example 1 and substituting 3,4-di(2-methoxy-ethoxy) aniline for 3,4-dimethoxyaniline in Step A, and 2,6-diaminotoluene for 1,3-diaminobenzene in Step C, Compound Ib-17 was prepared. MS 423 [M+H], HPLC: Rt=1.74 minutes Using the procedure described in Example 1 and substituting 3-(2-chloroethoxy)-4-methoxyaniline for 3,4-dimethoxyaniline in Step A, and 2,6-diaminotoluene for 1,3-diaminobenzene in Step C, Compound Ib-18 was prepared. MS 383 [M+H], HPLC: Rt=1.78 minutes Using the procedure described in Example 1 and substituting 3-N,N-dimethylaniline for 1,3-diaminobenzene in Step C, Compound Ib-53 was prepared. MS 349 [M+H], HPLC: Rt=2.48 minutes Example 4

Synthesis of Compound Ib-9

A mixture of 10-fluoro-11-methoxy-4-methyldibenzo[c,f]-2,7-naphthyridine-3,6-diamine (32 mg, 0.10 mmol), 2-(morpholin-4-yl)-ethylamine (26 mg, 0.20 mmol) and 1-methyl-pyrrolidin-2-one (3 mL) was heated to 200° C. in a microwave oven for 3 hours. The resultant reaction mixture was purified using HPLC to provide Compound Ib-9 (15 mg, 35%). MS 433 [M+H], HPLC: Rt=1.31 min Example 5

Synthesis of Compounds Ib-5 to Ib-8 and Ib-12 to Ib-15

Using the procedure described in Example 4 and substituting N-methyl-3-(N,N-dimethylamino)-propylamine for 2-(morpholin-4-yl)-ethylamine, Compound Ib-5 was prepared. MS 419 [M+H], HPLC: Rt=1.40 minutes Using the procedure described in Example 4 and substituting N-methyl-2-(N,N-dimethylamino)-ethylamine for 2-(morpholin-4-yl)-ethylamine, Compound Ib-6 was prepared. MS 405 [M+H], HPLC: Rt=1.39 minutes Using the procedure described in Example 4 and substituting 3-(1-methyl-piperazin-4-yl)-propylamine for 2-(morpholin-4-yl)-ethylamine, Compound Ib-7 was prepared. MS 460 [M+H], HPLC: Rt=1.31 minutes Using the procedure described in Example 4 and substituting 3-(morpholin-4-yl)-propylamine for 2-(morpholin-4-yl)-ethylamine, Compound Ib-8 was prepared. MS 447 [M+H], HPLC: Rt=1.32 minutes Using the procedure described in Example 4 and substituting 3-(pyrroldin-1-yl)-propylamine for 2-(morpholin-4-yl)-ethylamine, Compound Ib-12 was prepared. MS 431 [M+H], HPLC: Rt=1.35 minutes Using the procedure described in Example 4 and substituting 2-(pyrroldin-1-yl)-ethylamine for 2-(morpholin-4-yl)-ethylamine, Compound Ib-13 was prepared. MS 417 [M+H], HPLC: Rt=1.35 minutes Using the procedure described in Example 4 and substituting 2-(N,N-dimethylamino)-ethylamine for 2-(morpholin-4-yl)-ethylamine, Compound Ib-14 was prepared. MS 391 [M+H], HPLC: Rt=1.30 minutes Using the procedure described in Example 4 and substituting 3-(N,N-dimethylamino)-propylamine for 2-(morpholin-4-yl)-ethylamine, Compound Ib-15 was prepared. MS 405 [M+H], HPLC: Rt=1.31 minutes Example 6

Synthesis of Compound Ib-10

2-(Morpholin-4-yl)-ethanol (26 mg, 0.20 mmol) was diluted with DMF (2 mL) and to the resultant solution was added sodium hydride (8 mg, 0.2 mmol). The resultant reaction was allowed to stir at room temperature for 20 minutes, then 10-fluoro-11-methoxy-4-methyldibenzo[c,f]-2,7-naphthyridine-3,6-diamine (32 mg, 0.10 mmol) was added to the reaction mixture. The resultant reaction was heated to 70° C. and allowed to stir for 2 hours, then concentrated in vacuo to provide a crude residue, which was purified using HPLC to provide Compound Ib-10 (14 mg, 33%). MS 434 [M+H], HPLC: Rt=1.36 minutes Example 7

Synthesis of Compounds Ib-11, Ib-16, Ib-19 to Ib-35, Ib-42 to Ib-48, and Ib-50

Using the procedure described in Example 6 and substituting 3-(morpholin-4-yl)-propanol for 2-(morpholin-4-yl)-ethanol, Compound Ib-11 was prepared. MS 448 [M+H], HPLC: Rt=1.40 minutes Using the procedure described in Example 6 and substituting N-methyl-4-hydroxymethyl-piperidine for 2-(morpholin-4-yl)-ethanol, Compound Ib-16 was prepared. MS 432 [M+H], HPLC: Rt=1.44 minutes Using the procedure described in Example 6 and substituting 2-(azetidin-1-yl)-ethanol for 2-(morpholin-4-yl)-ethanol, Compound Ib-19.was prepared. MS 390 [M+H], HPLC: Rt=1.47 minutes Using the procedure described in Example 6 and substituting 2-(N,N-dimethyl)-ethanol for 2-(morpholin-4-yl)-ethanol, Compound Ib-20 was prepared. MS 392 [M+H], HPLC: Rt=1.40 minutes Using the procedure described in Example 6 and substituting 3-(N,N-dimethyl)-propanol for 2-(morpholin-4-yl)-ethanol, Compound Ib-21 was prepared. MS 406 [M+H], HPLC: Rt=1.44 minutes Using the procedure described in Example 6 and substituting 2-(pyrroldin-1-yl)-ethanol for 2-(morpholin-4-yl)-ethanol, Compound Ib-22 was prepared. MS 418 [M+H], HPLC: Rt=1.44 minutes Using the procedure described in Example 6 and substituting 2-(N,N-diethyl)-ethanol for 2-(morpholin-4-yl)-ethanol, Compound Ib-23 was prepared. MS 420 [M+H], HPLC: Rt=1.47 minutes Using the procedure described in Example 6 and substituting 2-(pyridin-2-yl)-ethanol for 2-(morpholin-4-yl)-ethanol, Compound Ib-24 was prepared. MS 426 [M+H], HPLC: Rt=1.60 minutes Using the procedure described in Example 6 and substituting 2-(N-methyl-pyrroldin-2-yl)-ethanol for 2-(morpholin-4-yl)-ethanol, Compound Ib-25 was prepared. MS 432 [M+H], HPLC: Rt=1.49 minutes Using the procedure described in Example 6 and substituting 2-(piperidin-1-yl)-ethanol for 2-(morpholin-4-yl)-ethanol, Compound Ib-26 was prepared. MS 432 [M+H], HPLC: Rt=1.48 minutes Using the procedure described in Example 6 and substituting 3-(N,N-diethyl)-propanol for 2-(morpholin-4-yl)-ethanol, Compound Ib-27 was prepared. MS 434 [M+H], HPLC: Rt=1.50 minutes Using the procedure described in Example 6 and substituting 2-(aziridin-1-yl)-ethanol for 2-(morpholin-4-yl)-ethanol, Compound Ib-28 was prepared. MS 446 [M+H], HPLC: Rt=1.53 minutes Using the procedure described in Example 6 and substituting 3-(piperidin-1-yl)-propanol for 2-(morpholin-4-yl)-ethanol, Compound Ib-29 was prepared. MS 446 [M+H], HPLC: Rt=1.51 minutes Using the procedure described in Example 6 and substituting 3-(N,N-dimethylamino)-propylamine for 2-(morpholin-4-yl)-ethanol, Compound Ib-30 was prepared. MS 449 [M+H], HPLC: Rt=1.33 minutes Using the procedure described in Example 6 and substituting 2-(indol-3-yl)-ethanol for 2-(morpholin-4-yl)-ethanol, Compound Ib-31 was prepared. MS 464 [M+H], HPLC: Rt=2.04 minutes Using the procedure described in Example 6 and substituting 2-(4-N,N-dimethylphenyl)-ethanol for 2-(morpholin-4-yl)-ethanol, Compound Ib-32 was prepared. MS 468 [M+H], HPLC: Rt=1.67 minutes Using the procedure described in Example 6 and substituting 2-(N-methylpiperidin-4-yl)-ethanol for 2-(morpholin-4-yl)-ethanol, Compound Ib-33 was prepared. MS 446 [M+H], HPLC: Rt=1.52 minutes Using the procedure described in Example 6 and substituting 3-hydroxymethyl-N-methylpiperidine for 2-(morpholin-4-yl)-ethanol, Compound Ib-34 was prepared. MS 432 [M+H], HPLC: Rt=1.49 minutes Using the procedure described in Example 6 and substituting 3-(pyrrolidin-1-yl-2-one)-propanol for 2-(morpholin-4-yl)-ethanol, Compound Ib-35 was prepared. MS 446 [M+H], HPLC: Rt=1.75 minutes Using the procedure described in Example 6 and substituting 3-methyl-1-butanol for 2-(morpholin-4-yl)-ethanol, Compound Ib-40 was prepared. MS 391 [M+H], HPLC: Rt=2.66 minutes Using the procedure described in Example 6 and substituting neopentyl alcohol for 2-(morpholin-4-yl)-ethanol, Compound Ib-41 was prepared. MS 405 [M+H], HPLC: Rt=2.72 minutes Using the procedure described in Example 6 and substituting 2-benzyloxy-ethanol for 2-(morpholin-4-yl)-ethanol, Compound Ib-42 was prepared. MS 469 [M+H], HPLC: Rt=2.59 minutes Using the procedure described in Example 6 and substituting 1-(benzyl-pyrroldin-2-yl)-methanol for 2-(morpholin-4-yl)-ethanol, Compound Ib-43 was prepared. MS 494 [M+H], HPLC: Rt=1.65 minutes Using the procedure described in Example 6 and substituting [1-(1-methyl-pyrrolidin-2-ylmethyl)-pyrroldin-2-yl]-methanol for 2-(morpholin-4-yl)-ethanol, Compound Ib-44 was prepared. MS 501 [M+H], HPLC: Rt=1.36 minutes Using the procedure described in Example 6 and substituting 2-cyclohexyl-ethanol for 2-(morpholin-4-yl)-ethanol, Compound Ib-45 was prepared. MS 417 [M+H], HPLC: Rt=2.21 minutes Using the procedure described in Example 6 and substituting 2-cyclopropyl-ethanol for 2-(morpholin-4-yl)-ethanol, Compound Ib-46 was prepared. MS 389 [M+H], HPLC: Rt=1.96 minutes Using the procedure described in Example 6 and substituting 2-ethoxyethanol for 2-(morpholin-4-yl)-ethanol, Compound Ib-47 was prepared. MS 393 [M+H], HPLC: Rt=2.22 minutes Example 8

Synthesis of Compound Ib-36

A mixture of 10,11-dimethoxy-4-methyldibenzo[c,f]-2,7-naphthyridine-3,6-diamine (1.0 g, 3.0 mmol), phthalic anhydride (0.46 g, 3.1 mmol) and acetic acid (10 mL) was heated to 115° C. and the resultant reaction was allowed to stir for 48 hours, then cooled to room temperature. The resultant reaction mixture was concentrated in vacuo and the resultant residue was diluted with ethyl acetate (250 mL). The resultant solution was washed with aqueous sodium hydroxide (1 N), then brine. The organic layer was collected, dried over sodium sulfate and concentrated in vacuo. The resultant residue was purified using flash column chromatography (silica gel with 3% methanol/methylene chloride eluent) to provide Compound Ib-36 as a yellow solid (1.0 g, 72%). MS 465 [M+H], HPLC: Rt=2.34 minutes Example 9

Synthesis of Compound 1-3

A mixture of Compound Ib-36 (from Example 8, 33 mg, 0.070 mmol), p-toluenesulfonyl chloride (22 mg, 0.11 mmol) and pyridine (1 mL) was heated to 60° C. and the resultant reaction was allowed to stir for 1 hour. The resultant reaction mixture was cooled to room temperature and concentrated in vacuo. The resultant residue was treated with hydrazine (0.5 mL in 1 mL ethanol) and the resultant reaction was allowed to stir for 18 hours at room temperature. The resultant reaction mixture was then purified using HPLC to provide Compound I-3 (10 mg, 44%). MS 320 [M+H]; $^1$H NMR (DMSO-d6): δ 9.34 (1H, s); 9.26 (1H, s); 8.79 (1H, d); 8.35 (1H, s); 7.63 (1H, s); 7.29 (1H, d); 5.86 (2H, br); 4.08 (3H, s); 4.01 (3H, s); 2.58 (3H, s). HPLC: Rt=1.82 minutes.

Example 10

Synthesis of Compound Ic-1

Compound Ib-36 (from Example 8, 46 mg, 0.10 mmol) was diluted with DMF (2 mL) and to the resultant solution was added iodomethane (21 mg, 0.15 mmol). The resultant reaction was heated to 60° C. and allowed to stir for 15 hours. The resultant reaction mixture was concentrated in vacuo to provide a crude residue which was treated with hydrazine (0.5 mL in 1 mL of ethanol) and the resultant reaction was allowed to stir at room temperature for 15 hours. The reaction mixture was then purified using HPLC to provide Compound Ic-1 (14 mg, 40%). MS 349 [M+H], HPLC: Rt=2.26 minutes Example 11

Synthesis of Compound Ib-1

4-Chloro-6,7-dimethoxy-quinoline-3-carbonitrile (from Example 1, Step C, 25 mg, 0.10 mmol) was diluted with DME (2 mL) and to the resultant solution was added (2-boc-aminophenyl) boronic acid (26 mg, 1.1 mmol), tetrakis-triphenylphosphinepalladium(0) (2 mg, 2% molar), and aqueous sodium carbonate (2.0 M, 0.2 mL). The resultant reaction was heated to 80° C. and allowed to stir for 16 hours. The reaction mixture was then cooled to room temperature and purified using HPLC to provide Compound Ib-1 (15 mg, 53% yield). MS 306 [M+H], HPLC: Rt=2.96 minutes Example 12

Synthesis of Compound Ib-39

A mixture of 10,11-dimethoxy-4-methyldibenzo[c,f]-2,7-naphthyridine-3,6-diamine (0.17 g, 0.50 mmol), 2 mL of acetic acid (2 mL), 0.8 mL of water (0.8 mL) and concentrated HCl (0.22 mL) was cooled to 0° C. and to the resultant solution was added dropwise an aqueous solution of sodium nitrite (76 mg, 1.1 mmol, in 0.3 mL water). The resultant reaction was allowed to stir at 0° C. for 30 minutes, then hypophosphorous acid (2.4 mL, 50 wt % solution in water) was added. The resultant reaction was allowed to stir at 0° C. for 8 hours then allowed to warm to room temperature. The reaction mixture was neutralized using aqueous sodium bicarbonate and the neutralized solution was extracted with ethyl acetate. The organic layer was collected, concentrated in vacuo and the resultant crude residue was purified using HPLC to provide Ib-39 as a solid (44 mg, 28%). MS 320 [M+H]; $^1$H NMR (DMSO-d6): δ 9.44 (1H, s); 8.61 (1H, d); 8.14 (1H, s); 7.61 (1H, s); 7.50 (1H, d); 7.31 (1H, m); 4.03 (3H, s); 4.02 (3H, s); 2.53 (3H, s). HPLC: Rt=2.42 minutes.

Example 13

Synthesis of Compound Ib-48

10-Fluoro-11-methoxy-4-methyldibenzo[c,f]-2,7-naphthyridine-3,6-diamine (16 mg, 0.050 mmol) was diluted with DMSO (1 mL) and to the resultant solution was added sodium hydroxide (10 mg, 0.25 mmol). The resultant reaction was heated to 80° C. and allowed to stir for 15 hours. The reaction was cooled to room temperature and the resultant reaction mixture was purified using HPLC to provide Compound Ib-48 (5.4 mg, 34% yield). MS 321 [M+H], HPLC: Rt=1.87 minutes.

Example 14

Synthesis of Compound Ib-49

A mixture of 10,11-dimethoxy-4-methyldibenzo[c,f]-2,7-naphthyridine-3,6-diamine (40 mg, 0.12 mmol), acetic acid (0.5 mL), water (0.2 mL) and concentrated HCl (0.06 mL) was cooled to 0° C. To the resultant solution was added dropwise an aqueous solution of sodium nitrite (19 mg, 0.28 mmol, in 1 mL water) and the resultant reaction was allowed to stir for 30 minutes at 0° C. To the resultant reaction mixture was added copper(I) chloride (15 mg, 0.15 mmol), then water (1.0 mL) and the resultant reaction was heated to 100° C. and allowed to stir for 1 hour. The reaction was then allowed to cool to room temperature, the reaction mixture was filtered, and the filtrate was concentrated in vacuo to provide a crude residue which was purified using HPLC to provide Compound Ib-49 (5.0 mg, 12%). MS 354 [M+H], HPLC: Rt=2.71 minutes.

Example 15

Synthesis of Compound Ib-50

Using the method described in Example 14, and substituting 20% aqueous sulfuric acid (2 mL) and toluene (4 mL) for copper (I) chloride and water, Compound Ib-50 was prepared. MS 336 [M+H], HPLC: Rt=2.02 minutes.

Example 16

Synthesis of Compound Ib-51

6-Amino-10,11-dimethoxy-4-methyldibenzo[c,f]-2,7-naphthyridin-3-ol (10 mg, 0.03 mmol) was diluted with DMSO (1 mL) and to the resultant solution was added dimethyl sulfate (6.0 mg, 0.047 mmol), then potassium carbonate (6 mg, 0.1 mmol). The resultant reaction was allowed to stir at room temperature for 15 hours, then the reaction mixture was purified using HPLC to provide Compound Ib-51 (2.4 mg, 22%). MS 350 [M+H], HPLC: Rt=2.39 minutes.

Example 17

Synthesis of Compound I-1

Using the method described in Example 16 and substituting 6-methoxy-10,11-dimethoxy-4-methyldibenzo[c,f]-2,7-naphthyridin-3-ol for 6-amino-10,11-dimethoxy-4-methyldibenzo[c,f]-2,7-naphthyridin-3-ol, Compound I-1 was prepared. MS 365 [M+H], HPLC: Rt=2.95 minutes Example 18

In vitro PDK-1 Inhibitory Activity For Illustrative Dibenzonaphthyridine Derivatives The ability of illustrative Dibenzonaphthyridine Derivatives to inhibit PDK-1 in vitro can be determined using the ELISA assay as decribed in Kobayashi et al., *Biochem. J.* 339:319-328 (1999) and Park et al., EMBO J. 18:3024-3033 (1999).

In this in vitro assay, PDK-1 kinase phosphorylates SGK1 on Threonine 256. After 17 minutes, the reaction is quenched via the addition of urea. The 6×HIS tagged SGK1 is then bound to 96 well Ni-NTA HisSorb plates and the phosphorylated SGK1 is detected using rabbit derived anti-phospho SGK antibody as the primary antibody and HRP coupled anti-rabbit antibody as the secondary antibody. HRP is then detected using a Chemiluminescent Substrate.

Table 3 shows PDK-1 inhibtion data for illustrative Dibenzonaphthyridine Derivatives that was obtained using the assay described above in Example 18.

TABLE 3

PDK-1 Inhibition Data for Illustrative Dibenzonaphthyridine Derivatives

| Compound | $IC_{50}$ (nM) |
|---|---|
| I-1 | 23837.00 |
| I-3 | 2503.00 |
| Ib-1 | 2402.67 |
| Ib-2 | 93.03 |
| Ib-3 | 273.00 |
| Ib-4 | 388.33 |
| Ib-5 | 1013.00 |
| Ib-6 | 1167.50 |
| Ib-7 | 555.50 |
| Ib-8 | 290.00 |
| Ib-9 | 295.50 |
| Ib-10 | 57.50 |
| Ib-11 | 121.50 |
| Ib-12 | 846.50 |
| Ib-13 | 3706.00 |
| Ib-14 | 2415.00 |
| Ib-15 | 971.50 |
| Ib-16 | 878.00 |
| Ib-17 | 275.00 |
| Ib-18 | 42.50 |
| Ib-19 | 482.00 |
| Ib-20 | 377.00 |
| Ib-21 | 196.50 |
| Ib-22 | 261.50 |
| Ib-23 | 347.00 |
| Ib-24 | 2864.67 |
| Ib-25 | 287.50 |
| Ib-26 | 324.00 |
| Ib-27 | 295.00 |
| Ib-28 | 350.33 |
| Ib-29 | 242.67 |
| Ib-30 | 280.67 |
| Ib-31 | 539.33 |
| Ib-32 | 667.25 |
| Ib-33 | 383.67 |
| Ib-34 | 1770.00 |
| Ib-35 | 111.00 |
| Ib-36 | 1725.00 |
| Ib-38 | 670.00 |
| Ib-39 | 258.00 |
| Ib-40 | 1182.00 |
| Ib-41 | 6436.00 |
| Ib-42 | 2438.00 |
| Ib-43 | 2975.00 |
| Ib-44 | 949.00 |
| Ib-45 | 4531.00 |
| Ib-46 | 212.00 |
| Ib-47 | 171.67 |
| Ib-48 | 1372.00 |
| Ib-49 | 2216.00 |
| Ib-50 | 46.00 |
| Ib-51 | 48.67 |
| Ic-1 | 36583.00 |

The results in Table 3 show that the Dibenzonaphthyridine Derivatives are effective at inhibiting PDK-1. Accordingly, Applicants believe that the Dibenzonaphthyridine Derivatives are useful for treating or preventing a proliferative disorder, such as cancer.

The present invention is not to be limited in scope by the specific embodiments disclosed in the examples or schemes, which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference in their entirety.

What is claimed is:

1. A compound having the formula

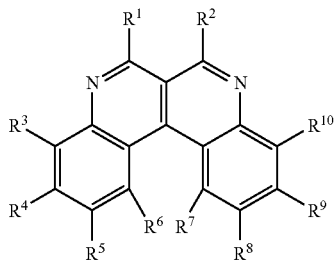

(I)

or a pharmaceutically acceptable salt thereof, wherein
$R^1$ is —OH, —O—$C_1$-$C_6$ alkyl, —$C_2$-$C_6$ alkenyl, —$C_2$-$C_6$ alkynyl, —N($R^{18}$)$_2$, —NH—O$R^{18}$ or —C(O)N($R^{18}$)$_2$;
$R^2$ is —H, —O—$C_1$-$C_6$ alkyl, -halo, —$C_2$-$C_6$ alkenyl, —$C_2$-$C_6$ alkynyl, —NH$R^{17}$, —N($R^{17}$)$_2$, —NH—O$R^{18}$ or —C(O)N($R^{18}$)$_2$, such that when $R^1$ is —OH or —O—$C_1$-$C_6$ alkyl, $R^2$ is hydrogen;
$R^3$, $R^4$, $R^5$, $R^6$, $R^7$, $R^8$, $R^9$ and $R^{10}$ are each independently —H, -halo, —OH, —SH, —N($R^{12}$)$_2$, —NHO$R^{12}$, —CN, —NO$_2$, —CF$_3$, —OCF$_3$, —$C_1$-$C_6$ alkyl, —$C_2$-$C_6$ alkenyl, —$C_2$-$C_6$ alkynyl, —$C_3$-$C_8$ cycloalkyl, —$C_3$-$C_8$ cycloalkenyl, -phenyl, -benzyl, —(CH$_2$)$_n$—O—$C_1$-$C_6$ alkyl, —O—$C_2$-$C_6$ alkenyl, —O—$C_2$-$C_6$ alkynyl, —O—phenyl, —S-phenyl, —NH—$C_1$-$C_6$ alkyl, —(CH$_2$)$_n$—C(O)—$R^{11}$, —(CH$_2$)$_n$—OC(O)—$R^{11}$, —(CH$_2$)$_n$—NHC(O)—$R^{11}$, —S—$C_1$-$C_6$ alkyl, —S(O)—$C_1$-$C_6$ alkyl, —SO$_2$—$C_1$-$C_6$ alkyl, —SO$_2$NH—$C_1$-$C_6$ alkyl, —SO$_2$NH—$C_2$-$C_6$ alkenyl, —SO$_2$NH—$C_2$-$C_6$ alkynyl, —Y—(CH$_2$)$_k$-M-CH($R^{14}$)$R^{15}$, —Y—(CH$_2$)$_g$—$R^{16}$, —Y—(CH$_2$)$_k$-M-(CH$_2$)$_p$—$R^{16}$, —Y—(CH$_2$)$_k$—(W)$_a$—(CH$_2$)$_q$—Z, —Y—(CH$_2$)$_p$—(Z)$_a$—(CH$_2$)$_q$—Z, or

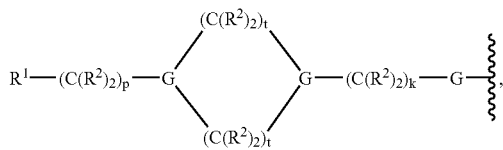

such that $R^3$, $R^4$, $R^5$, $R^6$, $R^7$, $R^8$, $R^9$ and $R^{10}$ are not simultaneously hydrogen;
$R^{11}$ is —H, —$C_1$-$C_6$ alkyl, —$C_2$-$C_6$ alkenyl, —$C_2$-$C_6$ alkynyl, -phenyl, —O—$C_1$-$C_6$ alkyl, —O—$C_2$-$C_6$ alkenyl, —O—$C_2$-$C_6$ alkynyl, —O—phenyl, —S-phenyl, —S—$C_1$-$C_6$ alkyl or —N($R^{12}$)$_2$;

each occurrence of $R^{12}$ is independently —H, —$C_1$-$C_6$ alkyl, —$C_2$-$C_6$ alkenyl, —$C_2$-$C_6$ alkynyl, -phenyl or -benzyl;
each occurrence of G is independently —O—, —S—, —(CH$_2$)—,

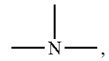

or —N($R^{13}$)—;
M is —O—, —N($R^{13}$)—, —N((C($R^{13}$)$_2$)$_p$N($R^{13}$)$_2$)— or —N((C($R^{13}$)$_2$)$_p$—O$R^{13}$)—;
W is —O— or —N($R^{13}$)—;
Y is —O—, —S—, —(CH$_2$)$_a$— or —N($R^{13}$)—;
Z is a -3- to 7-membered non-aromatic monocyclic heterocycle, -5- or 6-membered aromatic monocyclic heterocycle, or -8- to 12-membered bicyclic heterocycle, wherein a -3- to 7-membered non-aromatic monocyclic heterocycle may be unsubstituted or independently substituted on a ring carbon or ring nitrogen atom with one or more of —$R^{13}$, —N($R^{13}$)$_2$, —OH, —O$R^{13}$, —(C($R^{13}$)$_2$)$_s$O$R^{13}$ or —(C($R^{13}$)$_2$)$_s$N($R^{13}$)$_2$;
each occurrence of $R^{13}$ is independently —H, —$C_1$-$C_6$ alkyl, —CH$_2$-$C_2$-$C_6$ alkenyl, —CH$_2$—$C_2$-$C_6$ alkynyl, —$C_3$-$C_8$ cycloalkyl, —$C_3$-$C_8$ cycloalkenyl, -phenyl, —C(O)—$C_1$-$C_6$ alkyl or —C(O)—O—$C_1$-$C_6$ alkyl, such that when $R^{13}$ is -phenyl, the phenyl group may be unsubstituted or independently substituted with one or more of —OH, —CN, —NO$_2$, —CF$_3$, —$C_1$-$C_6$ alkyl, —NH($C_1$-$C_3$ alkyl), —N($C_1$-$C_3$ alkyl)$_2$, —(CH$_2$)$_a$-halo, —(CH$_2$)$_a$—O—$C_1$-$C_6$ alkyl, —(CH$_2$)$_a$—O—C(O)$C_1$-$C_6$ alkyl, —S—$C_1$-$C_6$ alkyl, —C(O)OH, —C(O)O—$C_1$-$C_6$ alkyl, —S-phenyl, —O-phenyl, -phenyl, -benzyl, —NH—(CH$_2$)$_a$-phenyl or —NHC(O)$C_1$-$C_6$ alkyl;
$R^{14}$ is —H, —(C($R^{13}$)$_2$)$_r$N($R^{13}$)$_2$ or —(C($R^{13}$)$_2$)$_r$O$R^{13}$;
$R^{15}$ is —H, —(C($R^{13}$)$_2$)$_r$N($R^{13}$)$_2$ or —(C($R^{13}$)$_2$)$_r$O$R^{13}$;
$R^{16}$ is —H, -halo, —N($R^{13}$)$_2$, —O$R^{13}$, —N($R^{13}$)$_3^+$ or —N($R^{13}$)—O$R^{13}$;
each occurrence of $R^{17}$ is independently —$C_1$-$C_6$ alkyl, —$C_2$-$C_6$ alkenyl, —$C_2$-$C_6$ alkynyl, -phenyl or benzyl;
each occurrence of $R^{18}$ is independently —H, —$C_1$-$C_6$ alkyl, —$C_2$-$C_6$ alkenyl, -$C_2$-$C_6$ alkynyl, -phenyl or benzyl;
a is 0 or 1;
g is an integer ranging from 1 to 6;
k is an integer ranging from 1 to 4;
n is an integer ranging from 0 to 6;
p is an integer ranging from 1 to 4;
q is an integer ranging from 0 to 4;
r is an integer ranging from 1 to 4;
s is an integer ranging from 1 to 6; and
each occurrence of t is independently an integer ranging from 1 to 3.

2. The compound of claim 1, wherein $R^1$ is —NH$_2$ and $R^2$ is —H.

3. The compound of claim 2, wherein $R^3$ is —$C_1$-$C_6$ alkyl.

4. The compound of claim 2, wherein $R^4$ —NH$_2$.

5. The compound of claim 2, wherein $R^4$ is —O—$C_1$-$C_6$ alkyl.

6. The compound of claim 2, wherein $R^4$ is —OH.

7. The compound of claim 2, wherein $R^8$ and $R^9$ are each —O—$C_1$-$C_6$ alkyl.

8. The compound of claim 2, wherein $R^2$, $R^5$, $R^6$, $R^7$ and $R^{10}$ are each —H.

9. The compound of claim 8, wherein $R^2$, $R^5$, $R^6$, $R^7$ and $R^{10}$ are each —H, $R^3$ is —$C_1$-$C_6$ alkyl, and $R^4$ is —$NH_2$.

10. The compound of claim 9, wherein $R^2$, $R^5$, $R^6$, $R^7$ and $R^{10}$ are each —H, $R^3$ is —$C_1$-$C_6$ alkyl, $R^4$ is —$NH_2$, and $R^8$ is —O—$C_1$-$C_6$ alkyl.

11. The compound of claim 10, wherein $R^2$, $R^5$, $R^6$, $R^7$ and $R^{10}$ are each —H, $R^3$ is —$C_1$-$C_6$ alkyl, $R^4$ is —$NH_2$, $R^8$ is —O—$C_1$-$C_6$ alkyl and $R^9$ is —O—$C_1$-$C_6$ alkyl. and $R^9$ is —O—$C_1$-$C_6$ alkyl.

12. The compound of claim 8, wherein $R^2$, $R^5$, $R^6$, $R^7$ and $R^{10}$ are each —H, $R^3$ is —$C_1$-$C_6$ alkyl, $R^4$ is —OH, and $R^8$ is —O—$C_1$-$C_6$ alkyl.

13. The compound of claim 12, wherein $R^2$, $R^5$, $R^6$, $R^7$ and $R^{10}$ are each —H, $R^3$ is —$C_1$-$C_6$ alkyl, $R^4$ is —OH, $R^8$ is —O—$C_1$-$C_6$ alkyl and $R^9$ is —O—$C_1$-$C_6$ alkyl.

14. The compound of claim 8, wherein $R^2$, $R^5$, $R^6$, $R^7$ and $R^{10}$ are each —H, $R^3$ is —$C_1$-$C_6$ alkyl, $R^4$ is —$OCH_3$, and $R^8$ is —O—$C_1$-$C_6$ alkyl.

15. The compound of claim 14, wherein $R^2$, $R^5$, $R^6$, $R^7$ and $R^{10}$ are each —H, $R^3$ is —$C_1$-$C_6$ alkyl, $R^4$ is —$OCH_3$, $R^8$ is —O—$C_1$-$C_6$ alkyl and $R^9$ is —O—$C_1$-$C_6$ alkyl.

16. The compound of claim 1 wherein at least one of $R^3$, $R^4$, $R^5$, $R^6$, $R^7$, $R^8$, $R^9$ and $R^{10}$ is

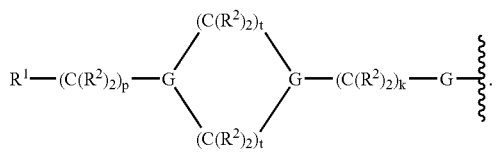

17. A composition comprising an effective amount of the compound or a pharmaceutically acceptable salt of the compound of claim 1 and a physiologically acceptable vehicle.

18. A method for treating cancer selected from the group consisting of brain cancer, colon cancer, leukemia, prostate cancer and breast cancer, the method comprising administering to a subject in need thereof an effective amount of the compound or a pharmaceutically acceptable salt of the compound of claim 1.

19. The method of claim 18, further comprising the administration of another anticancer agent.

20. The compound of claim 1, wherein the compound is:
10,11-dimethoxydibenzo[c,f]-2,7-naphthyridin-6-amine;
10,11-dimethoxy-4-methyldibenzo[c,f]-2,7-naphthyridine-3,6-diamine;
10,11-diethoxy-4-methyldibenzo[c,f]-2,7-naphthyridine-3,6-diamine;
10-fluoro-11-methoxy-4-methyldibenzo[c,f]-2,7-naphthyridine-3,6-diamine;
$N^{10}$-[3-(dimethylamino)propyl]-11-methoxy-$N^{10}$,4-dimethyldibenzo[c,f]-2,7-naphthyridine-3,6,10-triamine;
$N^{10}$-[2-(dimethylamino)ethyl]-11-methoxy-$N^{10}$,4-dimethyldibenzo[c,f]-2,7-naphthyridine-3,6,10-triamine;
11-methoxy-4-methyl-$N^{10}$-[3-(4-methylpiperazin-1-yl)propyl]dibenzo[c,f]-2,7-naphthyridine-3,6,10-triamine;
11-methoxy-4-methyl-$N^{10}$-(3-morpholin-4-ylpropyl)dibenzo[c,f]-2,7-naphthyridine-3,6,10-triamine;
11-methoxy-4-methyl-$N^{10}$-(2-morpholin-4-ylethyl)dibenzo[c,f]-2,7-naphthyridine-3,6,10-triamine;
11-methoxy-4-methyl-10-(2-morpholin-4-ylethoxy)dibenzo[c,f]-2,7-naphthyridine-3,6-diamine;
11-methoxy-4-methyl-10-(3-morpholin-4-ylpropoxy)dibenzo[c,f]-2,7-naphthyridine-3,6-diamine;
11-methoxy-4-methyl-$N^{10}$-(3-pyrrolidin-1-ylpropyl)dibenzo[c,f]-2,7-naphthyridine-3,6,10-triamine;
11-methoxy-4-methyl-$N^{10}$-(2-pyrrolidin-1-ylethyl)dibenzo[c,f]-2,7-naphthyridine-3,6,10-triamine;
$N^{10}$-[2-(dimethylamino)ethyl]-11-methoxy-4-methyldibenzo[c,f]-2,7-naphthyridine-3,6,10-triamine;
$N^{10}$-[3-(dimethylamino)propyl]-11-methoxy-4-methyldibenzo[c,f]-2,7-naphthyridine-3,6,10-triamine;
11-methoxy-4-methyl-10-[(1-methylpiperidin-4-y1)methoxy]dibenzo[c,f]-2,7-naphthyridine-3,6-diamine;
10,11-bis(2-methoxyethoxy)-4-methyldibenzo[c,f]-2,7-naphthyridine-3,6-diamine;
10-(2-chloroethoxy)-11-methoxy-4-methyldibenzo[c,f]-2,7-naphthyridine-3,6-diamine;
10-(2-aziridin-1-ylethoxy)-11-methoxy-4-methyldibenzo[c,f]-2,7-naphthyridine-3,6-diamine;
10-[2-(dimethylamino)ethoxy]-11-methoxy-4-methyldibenzo[c,f]-2,7-naphthyridine-3,6-diamine;
10-[3-(dimethylamino)propoxy]-11-methoxy-4-methyldibenzo[c,]1-2,7-naphthyridine-3,6-diamine;
11-methoxy-4-methyl-10-(2-pyrrolidin-1-ylethoxy)dibenzo[c,f]-2,7-naphthyridine-3,6-diamine;
10-[2-(diethylamino)ethoxy]-11-methoxy-4-methyldibenzo[c,f]-2,7-naphthyridine-3,6-diamine;
11-methoxy-4-methyl-10-(2-pyridin-2-ylethoxy)dibenzo[c,f]-2,7-naphthyridine-3,6-diamine;
11-methoxy-4-methyl-10-[2-(1-methylpyrrolidin-2-yl)ethoxyl]dibenzo[c,f]-2,7-naphthyridine-3,6-diamine;
11-methoxy-4-methyl-10-(2-piperidin-1-ylethoxy)dibenzo[c,f]-2,7-naphthyridine-3,6-diamine
10-[3-(diethylamino)propoxy]-11-methoxy-4-methyldibenzo[c,f]-2,7-naphthyridine-3,6-diamine;
10-(2-azepan-1-ylethoxy)-11-methoxy-4-methyldibenzo[c,f]-2,7-naphthyridine-3,6-diamine;
11-methoxy-4-methyl-10-(3-piperidin-1-ylpropoxy)dibenzo[c,f]-2,7-naphthyridine-3,6-diamine;
10-{2-[[2-(dimethylamino)ethyl](methyl)amino]ethoxy}-11-methoxy-4-methyldibenzo[c,f]-2,7-naphthyridine-3,6-diamine;
10-[2-(1H-indol-3-yl)ethoxy]-11-methoxy-4-methyldibenzo[c,f]-2,7-naphthyridine-3,6diamine;
10-{2-[4-(dimethylamino)phenyl]ethoxy}-11-methoxy-4-methyldibenzo[c,f]-2,7-naphthyridine-3,6-diamine;
11-methoxy-4-methyl-10-[2-(1-methylpiperidin-4-yl)ethoxy]dibenzo[c,f]-2,7-naphthyridine-3,6-diamine;
11-methoxy-4-methyl-10-[(1-methylpiperidin-3-yl)methoxy]dibenzo[c,f]-2,7-naphthyridine-3,6-diamine;
1-{3-[(7,10-diamino-2-methoxy-9-methyldibenzo[c,f]-2,7-naphthyridin-3-yl)oxy]propyl}pyrrolidin-2-one;
2-(6-amino-10,11-dimethoxy-4-methyldibenzo[c,f]-2,7-naphthyridin-3-yl)-1H-isoindole-1,3(2H)-dione;
10,11-dimethoxy-4-methyldibenzo[c,f]-2,7-naphthyridin-3-amine;
10,11-dimethoxy-$N^1$,$N^1$-dimethyldibenzo[c,f]-2,7-naphthyridine-1,6-diamine;
10,11-dimethoxydibenzo[c,f]-2,7-naphthyridine-3,6-diamine;
2,3-dimethoxydibenzo[c,f]-2,7-naphthyridine;
10,11-dimethoxy-4-methyldibenzo[c,f]-2,7-naphthyridin-6-amine;
11-methoxy-4-methyl-10-(3-methylbutoxy)dibenzo[c,f]-2,7-naphthyridine-3,6-diamine;
10-(3,3-dimethylbutoxy)-11-methoxy-4-methyldibenzo[c,f]-2,7-naphthyridine-3,6-diamine 10-[3-(benzyloxy)propoxy]-11-methoxy-4-methyldibenzo[c,f]-2,7-naphthyridine-3,6-diamine;

10-{[(2S)-1-benzylpyrrolidin-2-yl]methoxy}-11-methoxy-4-methyldibenzo[c,f]-2,7-naphthyridine-3,6-diamine;

11-methoxy-4-methyl-10-[((2S)-1-{[(2S)-1-methylpyrrolidin-2-yl]methyl}pyrrolidin-2-yl)methoxy]dibenzo[c,f]-2,7-naphthyridine-3,6-diamine;

10-(2-cyclopentylethoxy)-11-methoxy-4-methyldibenzo[c,f]-2,7-naphthyridine-3,6-diamine;

10-(2-cyclopropylethoxy)-11-methoxy-4-methyldibenzo[c,f]-2,7-naphthyridine-3,6-diamine;

10,11-dimethoxy-N6,4-dimethyldibenzo[c,f]-2,7-naphthyridine-3,6-diamine;

10-(2-ethoxyethoxy)-11-methoxy-4-methyldibenzo[c,f]-2,7-naphthyridine-3,6-diamine;

7,10-diamino-2-methoxy-9-methyldibenzo[c,f]-2,7-naphthyridin-3-ol;

3-chloro-10,11-dimethoxy-4-methyldibenzo[c,f]-2,7-naphthyridin-6-amine;

6-amino-10,11-dimethoxy-4-methyldibenzo[c,f]-2,7-naphthyridin-3-ol;

3,10,11-trimethoxy-4-methyldibenzo[c,f]-2,7-naphthyridin-6-amine;

2,3,7,10-tetramethoxy-9-methyldibenzo[c,f]-2,7-naphthyridine;

10,11-dimethoxy-4-methyldibenzo[c,f]-2,7-naphthyridine-3,6-diol;

10-amino-3-methoxy-9-methyldibenzo[c,f]-2,7-naphthyridin-2-ol; or 11-methoxy-10-(2-methoxyethoxy)-4-methyldibenzo[c,f]-2,7-naphthyridine-3,6-diamine, or a pharmaceutically acceptable salt thereof.

21. A composition comprising an effective amount of the compound or a pharmaceutically acceptable salt of the compound of claim 20 and a physiologically acceptable vehicle.

22. A method for treating cancer selected from the group consisting of brain cancer, colon cancer, leukemia, prostate cancer and breast cancer, the method comprising administering to a subject in need thereof an effective amount of the compound or a pharmaceutically acceptable salt of the compound of claim 20.

23. The method of claim 18, wherein the subject is a human.

24. A method for making a compound of claim 1, comprising heating a compound of formula 4

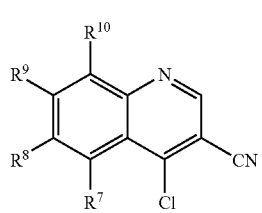

in the presence of a compound of formula 5

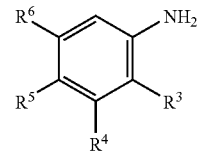

the compounds thereby reacting to form a compound of claim 1, wherein $R^1$ is —$NH_2$ and $R^2$ is —H.

25. The method of claim 24, wherein the solvent is ortho dichlorobenzene, diphenyl ether, polyethylene glycol, nitrobenzene, or ethoxyethanol.

26. The method of claim 24, wherein the solvent is ethoxyethanol.

27. The method of claim 24, further comprising using a proton catalyst.

28. The method of claim 27, wherein the catalyst comprises pyridine hydrochloride, para-toluene sulfonic acid, or PPTS, or a combination thereof.

29. A method for making a compound of claim 1, comprising applying microwave radiation to a compound of formula 4

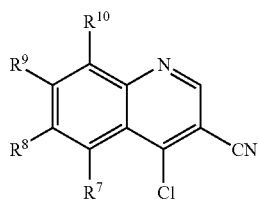

in the presence of a compound of formula 5

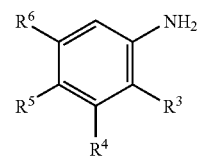

in a solvent, the compounds thereby reacting to form a compound of claim 1, wherein $R^1$ is —$NH_2$ and $R^2$ is —H.

30. The method of claim 29, wherein the solvent is ortho dichlorobenzene, diphenyl ether, polyethylene glycol, nitrobenzene, or ethoxyethanol.

31. The method of claim 29, wherein the solvent is ethoxyethanol.

32. The method of claim 29, further comprising using a proton catalyst.

33. The method of claim 32, wherein the catalyst comprises pyridine hydrochloride, para-toluene sulfonic acid, or PPTS, or a combination thereof.

34. The method of claim 18, wherein the subject is an animal.

35. A method for inhibiting PDK-1 in a cell, comprising contacting a compound of claim 1 to a cell, wherein the cell expresses PDK-1.

36. The method of claim 35, wherein the cell is in vitro.

37. The method of claim 35, wherein the cell is a cancer cell.

* * * * *